US012121359B2

(12) United States Patent
Saleh et al.

(10) Patent No.: US 12,121,359 B2
(45) Date of Patent: *Oct. 22, 2024

(54) MOBILE ECG GAME CONTROLLER APPARATUS

(71) Applicant: AliveCor, Inc., Mountain View, CA (US)

(72) Inventors: Ahmad N. Saleh, San Jose, CA (US); Sean Cohen, Mountain View, CA (US)

(73) Assignee: ALIVECOR, INC., Mountain View, CA (US)

( * ) Notice: Subject to any disclaimer, the term of this patent is extended or adjusted under 35 U.S.C. 154(b) by 646 days.

This patent is subject to a terminal disclaimer.

(21) Appl. No.: 17/234,558

(22) Filed: Apr. 19, 2021

(65) Prior Publication Data

US 2021/0236039 A1    Aug. 5, 2021

Related U.S. Application Data

(63) Continuation-in-part of application No. 16/440,738, filed on Jun. 13, 2019, now Pat. No. 11,103,175, (Continued)

(51) Int. Cl.
*A61B 5/316*    (2021.01)
*A61B 5/00*    (2006.01)
(Continued)

(52) U.S. Cl.
CPC ............ *A61B 5/316* (2021.01); *A61B 5/0006* (2013.01); *A61B 5/0015* (2013.01); *A61B 5/002* (2013.01);
(Continued)

(58) Field of Classification Search
CPC ................. A61B 5/316; A61B 5/327
(Continued)

(56) References Cited

U.S. PATENT DOCUMENTS

2014/0073979 A1    3/2014    Inciardi et al.
2014/0228665 A1*   8/2014    Albert .................. A61B 5/0245
                                        600/384

FOREIGN PATENT DOCUMENTS

WO    2011006356 A1    1/2011
WO    2012158190 A1    11/2012
(Continued)

OTHER PUBLICATIONS

Notification of First Office Action from related Chinese Patent Application No. 201980019802.8 mailed on Aug. 31, 2023 (18 pages including translation).

*Primary Examiner* — Nadia A Mahmood
(74) *Attorney, Agent, or Firm* — WOMBLE BOND DICKINSON (US) LLP

(57) ABSTRACT

Embodiments of the present disclosure are directed to an electrocardiogram (ECG) monitoring device embedded into the construct of a controller (e.g., video game controller, steering wheel etc.) to monitor a user's heart health and diagnose various conditions (e.g., AFib, tachycardia, bradycardia, etc.). The controller may comprise a set of electrodes including electrodes to contact the user's hands and one or more electrodes on the back of the controller that can be used to contact the user's extremities as a 3rd contact point to provide additional leads for higher accuracy ECG sensing. The set of electrodes may be positioned at locations on the controller where the user's hands are relatively stable, thus minimizing motion artifacts caused by muscular movement (thereby allowing for signal stability and longevity).

18 Claims, 22 Drawing Sheets

Related U.S. Application Data which is a continuation of application No. 15/923,699, filed on Mar. 16, 2018, now Pat. No. 10,342,444, which is a continuation-in-part of application No. 15/721,038, filed on Sep. 29, 2017, now Pat. No. 9,986,925, which is a continuation of application No. 15/140,072, filed on Apr. 27, 2016, now Pat. No. 9,833,158, which is a continuation of application No. 14/254,310, filed on Apr. 16, 2014, now Pat. No. 9,351,654, which is a continuation-in-part of application No. 13/108,738, filed on May 16, 2011, now abandoned, which is a continuation-in-part of application No. 12/796,188, filed on Jun. 8, 2010, now Pat. No. 8,509,882.

(51) Int. Cl.

| | | |
|---|---|---|
| A61B 5/0245 | (2006.01) | |
| A61B 5/25 | (2021.01) | |
| A61B 5/327 | (2021.01) | |
| A61B 5/332 | (2021.01) | |
| A61B 5/333 | (2021.01) | |
| A61B 5/339 | (2021.01) | |
| A61B 5/349 | (2021.01) | |
| G06Q 50/22 | (2018.01) | |
| A61B 5/0205 | (2006.01) | |

(52) U.S. Cl.
CPC .......... *A61B 5/0022* (2013.01); *A61B 5/0245* (2013.01); *A61B 5/25* (2021.01); *A61B 5/327* (2021.01); *A61B 5/332* (2021.01); *A61B 5/333* (2021.01); *A61B 5/339* (2021.01); *A61B 5/349* (2021.01); *A61B 5/6898* (2013.01); *A61B 5/7225* (2013.01); *G06Q 50/22* (2013.01); *A61B 5/0205* (2013.01); *A61B 5/7257* (2013.01); *A61B 2560/0412* (2013.01)

(58) Field of Classification Search
USPC ....................................................... 600/523
See application file for complete search history.

(56) References Cited

FOREIGN PATENT DOCUMENTS

| | | |
|---|---|---|
| WO | 2013155196 A2 | 10/2013 |
| WO | 2016073202 A1 | 5/2016 |
| WO | 2018035258 A1 | 2/2018 |

* cited by examiner

MOBILE ECG GAME CONTROLLER APPARATUS

CROSS-REFERENCE TO RELATED APPLICATIONS

This application is a continuation-in-part of U.S. patent application Ser. No. 16/440,738, filed Jun. 13, 2019, which is a continuation of U.S. patent application Ser. No. 15/923,699, filed Mar. 16, 2018, now U.S. Pat. No. 10,342,444, which is a continuation-in-part of U.S. patent application Ser. No. 15/721,038, filed Sep. 29, 2017, now U.S. Pat. No. 9,986,925, which is a continuation of U.S. patent application Ser. No. 15/140,072, filed Apr. 27, 2016, now U.S. Pat. No. 9,833,158, which is a continuation of U.S. patent application Ser. No. 14/254,310, filed Apr. 16, 2014, now U.S. Pat. No. 9,351,654, which is a continuation-in-part of U.S. patent application Ser. No. 13/108,738, filed May 16, 2011, which is a continuation-in-part of U.S. patent application Ser. No. 12/796,188, filed Jun. 8, 2010, now U.S. Pat. No. 8,509,882.

This application is also a continuation-in-part of U.S. patent application Ser. No. 16/440,738, filed Jun. 13, 2019, which is a continuation of U.S. patent application Ser. No. 15/923,699, filed Mar. 16, 2018, now U.S. Pat. No. 10,342,444, which is a continuation-in-part of U.S. patent application Ser. No. 15/486,777, filed Apr. 13, 2017, now Publication US-2017-0215755, which is a continuation of U.S. patent application Ser. No. 13/964,490, filed Aug. 12, 2013, now U.S. Pat. No. 9,649,042, which is a divisional of U.S. patent application Ser. No. 12/796,188, filed Jun. 8, 2010, now U.S. Pat. No. 8,509,882, each of which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The prior art includes numerous systems wherein ECG data or the like is monitored and/or transmitted from a patient to a particular doctor's office or health service center. For example, U.S. Pat. No. 5,735,285 discloses use of a handheld device that converts a patient's ECG signal into a frequency modulated audio signal that may then be analyzed by audio inputting via a telephone system to a selected hand-held computer device or to a designated doctor's office. Similarly, U.S. Pat. No. 6,264,614 discloses a heart monitor, which is manipulated by the patient to sense a biological function such as a heart beat, and outputs an audible signal to a computer microphone. The computer processes the audible signal and sends resulting data signals over a network or Internet. U.S. Pat. No. 6,685,633 discloses a heart monitor that a patient can hold against his or her chest. The device outputs an audible signal responsive to the function or condition, such as the beating of the heart, to a microphone connected to a computer. Each of these audio transmissions is limited to transmission of audible sound. In other words, frequency modulated sound transmission at carrier frequencies above that heard by humans, i.e. above 17 kHz, was not contemplated.

U.S. Pat. App. Publication No. 2004/0220487 discloses a system with ECG electrodes which sense ECG electrical signals which are combined and amplitude modulated. The composite signal is transmitted via wire or wirelessly to the sound port in a computing device. A digital band pass filter having a pass band from 19 kHz to 21 kHz is considered; however, there is no consideration of demodulation means at this frequency range using commercially available computing devices. Additionally, the use of sound waves to effect transmission is not contemplated.

U.S. Pat. App. Publication No. 2010/0113950 discloses an electronic device having a heart sensor including several leads for detecting a user's cardiac signals. The leads are coupled to interior surfaces of the electronic device housing to hide the sensor from view. Using the detected signals, the electronic device can then identify or authenticate the user.

U.S. Pat. No. 6,820,057 discloses a system to acquire, record, and transmit ECG data wherein the ECG signals are encoded in a frequency modulated audio tone having a carrier tone in the audio range. However, there is no real consideration of carrier frequencies above about 3 kHz, no consideration of carrier frequencies above the audible, and no consideration of demodulation methods at higher carrier frequencies.

Limitations of the prior art utilizing transtelephonic and audible acoustic signals include a signal to noise ratio that is diminished by talking or any other noisy activity in the vicinity, thus potentially jeopardizing the integrity of the heart monitoring data signals. Additionally, the audible signals can be heard by anyone in the vicinity of the computer and heart monitor, which can be bothersome to the user as well as to others in the vicinity. Other applications fail to provide a reliable, inexpensive personal monitoring device that is readily compatible with existing computing devices such as smartphones. It would be advantageous if these issues were addressed in a personal monitoring device transmitting real time physiological data.

DETAILED DESCRIPTION

Before explaining at least one embodiment of the invention in detail, it is to be understood that the invention is not limited in its application to the details of construction, experiments, exemplary data, and/or the arrangement of the components set forth in the following description. The invention is capable of other embodiments or of being practiced or carried out in various ways. Also, it is to be understood that the terminology employed herein is for purpose of description and should not be regarded as limiting.

In the following detailed description of embodiments of the disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

Figure 1:
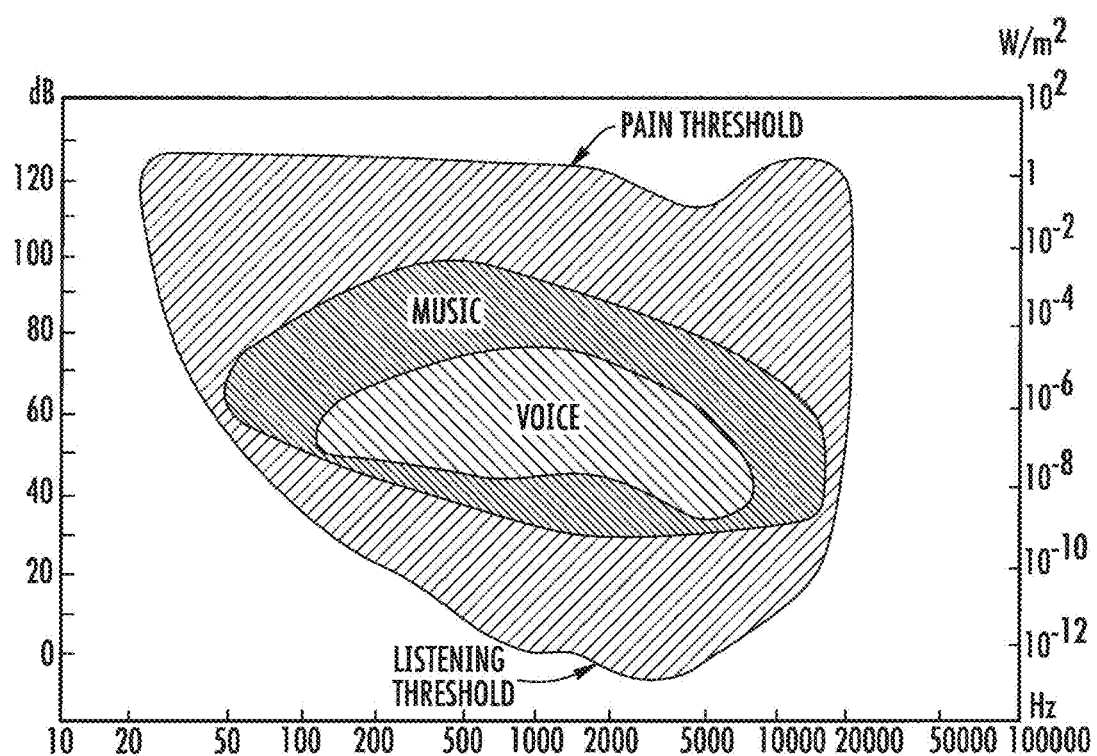
FIG. 1 is a pictorial representation of the human range and thresholds of hearing from http://en.labs.wikimedia.org/wiki/Acoustics.
Figure 2:
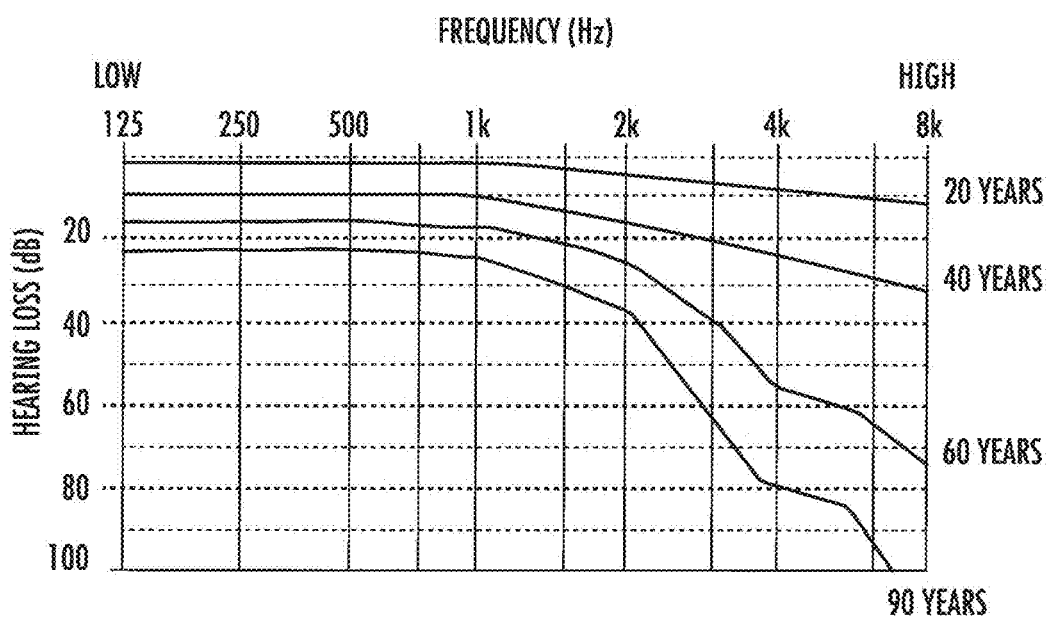
FIG. 2 is a pictorial representation of hearing loss with age from www.neuroreille.com/promenade/english/audiometry/audiometry.htm.

The human hearing range is often referred to as 20 Hz to 20 kHz. A maximum aural range in children, under ideal laboratory conditions, is actually as low as 12 Hz and as high as 20 kHz. However, as shown in FIG. 1, the threshold frequency, i.e. the minimum intensity detectable, rises rapidly to the pain threshold between 10 kHz to 20 kHz. Thus, sounds above about 16 kHz must be fairly intense to be heard. Almost immediately from birth, the threshold sound level for these higher frequencies increases. As shown in FIG. 2, an average 20 year old has lost about 10 dB in the 8 kHz range, while at age 90, the average person has lost over 100 dB at this frequency.

An example product using very high frequency sound is the Mosquito alarm, a controversial device emitting an intentionally annoying 17.4 kHz alarm and used to discourage younger people from loitering. Due to adult hearing loss at this frequency, it is typically heard only by people less than 25 years of age. Similarly, students make use of the adult hearing loss by using "mosquito" ringtones in the 15-17 kHz on their cell phones during school. The students can hear the "mosquito" ringtones while their adult teachers cannot. The term "ultrasonic" typically means above the range perceived by humans. However, as demonstrated, the upper limit of hearing frequency varies with individuals and with age generally. Because of the differences in this upper limit, the term "ultrasonic" is defined herein and in the appending claims to refer to "sound frequencies of 17 kHz or greater."

Figure 3:
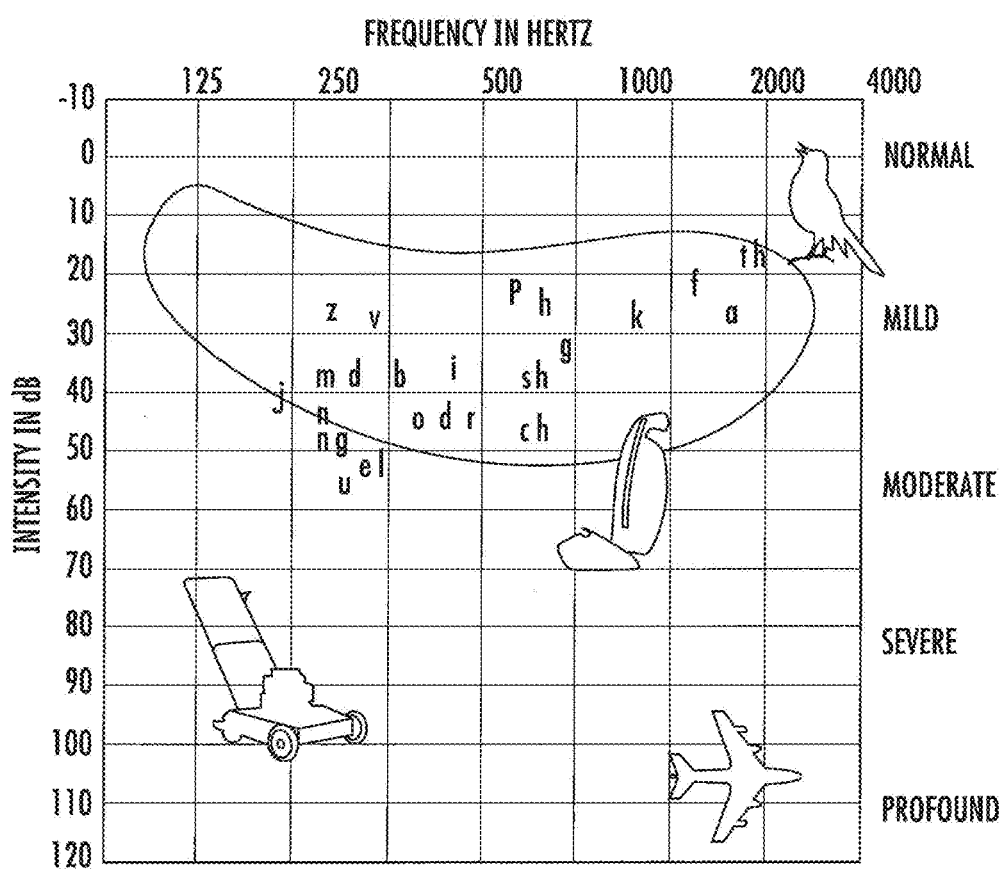
FIG. 3 is an audiogram illustrating the intensity and frequency of common sounds from www.hearinglossky.org/hlasurvival1.html.

Interestingly, however, there is very little ambient sound or noise above about 10 kHz. Referring to FIG. 3, most everyday sounds occur at frequencies below about 4 kHz. Thus, use of signals in the ultrasonic range is not only silent to those around, but also provides a very desirable signal to noise ratio (SNR).

Acoustic engineers safely assume that any frequency above about 20 kHz will have no effect on the perceived sound and they filter everything above this range. Sounds below 20 kHz but still in the ultrasonic range are of little concern, and standard sampling procedures have been established accordingly. It is generally understood that sampling an analog signal, whether a radio signal or audible sound signal, requires a sampling frequency $f_s$ such that $f_s/2 > f$, wherein f is the sinusoid frequency. For this reason, sound systems are designed to sample the sound at the now standard sample rate of 44.1 kHz, set somewhat higher than the calculated Nyquist-Shannon sampling rate of 40 kHz for a 20 kHz sound upper limit. Actual demodulation of an FM narrow band signal in the ultrasonic range, using existing demodulation procedures, computers, telephones, cell phones, stereo sound systems, etc., would result in very poor reproduction of the original signal. This is unfortunate because, as discussed above, a carrier signal in the ultrasonic range would also have a very low signal to noise ratio due to the fact that there is very little natural "noise" at these higher frequencies.

Application of ECG technology is useful in many situations where a user may interact (e.g., hold, touch, or otherwise make contact) with a device for extended periods of time. One example is the video game context, as the controller for a video game console is handheld for relatively large periods at a time, which provides the opportunity for live ECG updates during those periods of time when the user is handling the controller. The video game controller is also a stable data acquisition point as the user grips the controller tightly with both hands. The form factor of a video game controller also provides ample space for the microcontroller, sensors, and other necessary hardware components.

There are numerous other examples of devices that provide similar opportunity for integration of ECG technology such as a steering wheel, a television remote control, a computer mouse, and bicycle (or any other exercise equipment) handle bars or grips, among others. These devices may benefit from integration of ECG and other similar technologies as determining whether a user is undergoing a heart or other health condition during activities related to those devices can be important, and even life-saving in some situations.

Embodiments of the present disclosure are directed to an electrocardiogram (ECG) monitoring device embedded into the construct of a controller (e.g., video game controller, steering wheel etc.) to monitor a user's heart health and diagnose various conditions (e.g., AFib, tachycardia, bradycardia, etc.). The controller may comprise a set of electrodes including electrodes to contact the user's hands and perform a single lead ECG. Additionally, the set of electrodes may comprise another electrode positioned on the controller so as to contact a third extremity of the user, thereby providing a third contact point to provide additional leads for higher accuracy ECG sensing (e.g., a 6-lead ECG). The set of electrodes may be positioned at locations on the controller where the user's hands are relatively stable, thus minimizing motion artifacts caused by muscular movement (and allowing for signal stability and longevity). A converter assembly may frequency modulate the electrical signal (corresponding to heart activity of the user) output by the set of electrodes and transmit the modulated signal to a computing device for diagnostics, display, and other purposes.

Figure 4:
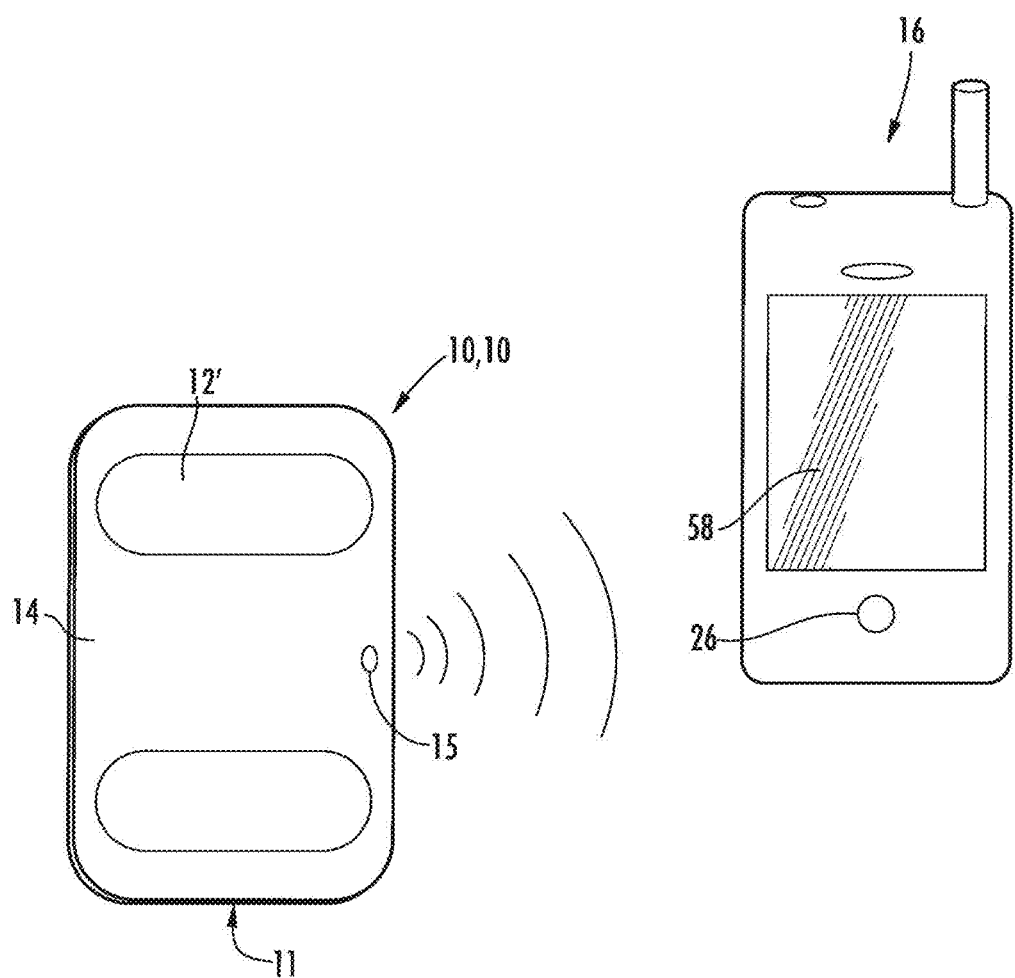
FIG. 4 is a schematic representation of an embodiment of a personal monitoring device transmitting to a computing device.
Figure 5:
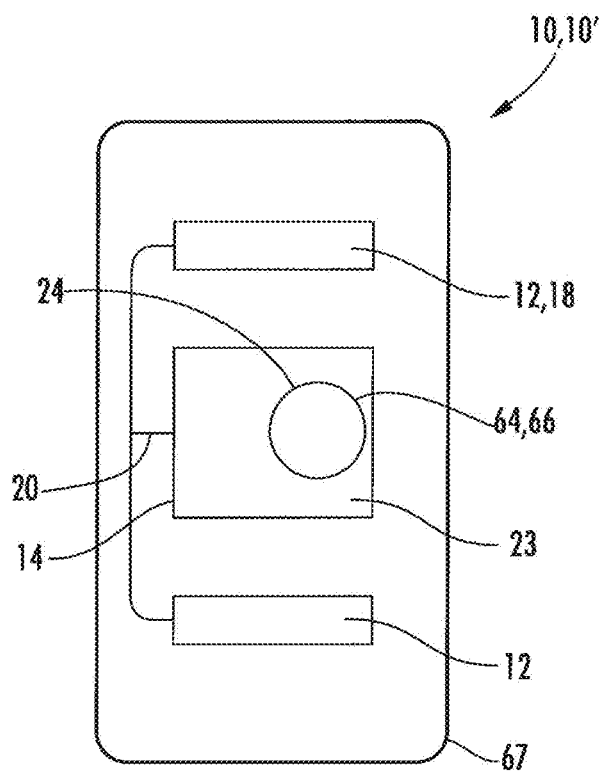
FIG. 5 is a schematic representation of another embodiment of a personal monitoring device of the present invention.

Other embodiments provide a personal monitoring device 10, embodiments of which are shown schematically in FIG. 4 and FIG. 5. The acquisition electronics 11 of the monitoring device 10 includes a sensor assembly 12 configured to sense physiological signals upon contact with a user's skin. The sensor assembly 12 produces electrical signals representing the sensed physiological signals, which input to a converter assembly 14, integrated with the sensor assembly 12. Converter assembly 14 converts the electrical signals generated by the sensor assembly 12 to a frequency modulated ultrasonic signal which is output by ultrasonic transmitter 24. In one embodiment, the frequency modulated ultrasonic signal has a carrier frequency in the range of from about 18 kHz to about 24 kHz. In another embodiment, the frequency modulated ultrasonic signal has a carrier frequency in the range of from about 20 kHz to about 24 kHz.

The sensor assembly 12 can include any suitable sensor operative to detect a physiological signal that a user desires to monitor. Nonlimiting examples of such physiological signals include, but are not limited to, respiration, heart beat, heart rate, electrocardiogram (ECG), electromyogram (EMG), electrooculogram (EOG), pulse oximetry, photoplethysmogram (PPG) and electroencephalogram (EEG).

Figure 6:
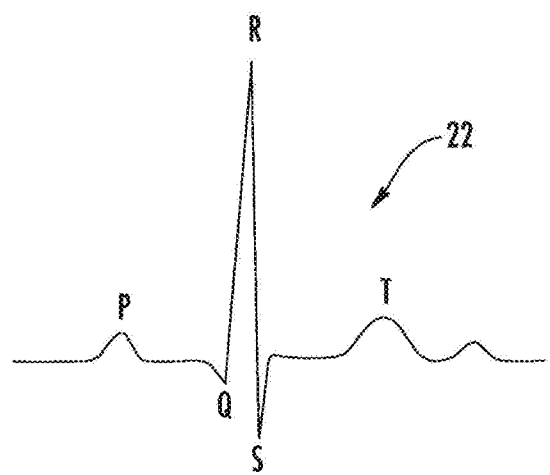
FIG. 6 is an example of graphical ECG representation.

A respiration detector can be a conventional microphone assisted stethoscope 12'. Heart beat and heart rate can be detected as well using a conventional microphone assisted stethoscope 12', or by using an electrode assembly 18 to sense electrical signals generated by the heart over time. Such electrodes 18 can also be used to detect the electrical activity of the heart over time for electrocardiograman ECG is a measurement of the small electrical changes on the skin generated when the heart muscle depolarizes during each heart beat. The output from a pair of electrodes 18 is known as a lead 20. Small rises and falls in the voltage between two electrodes placed on either side of the heart can be processed to produce a graphical ECG representation 22 such as the example ECG shown in FIG. 6.

Electromyography (EMG) detects the electrical potential generated by muscle cells when the cells are electrically or neurologically activated. The signals can be analyzed to detect medical abnormalities. Electrooculography (EOG) is a technique for measuring the resting potential of the retina. Usually, pairs of electrodes 18 are placed either above and below the eye, or to the left and right of the eye, and a potential difference measurement is a measure for the eye position.

The oxygenation of a person's hemoglobin can be monitored indirectly in a noninvasive manner using a pulse oximetry sensor, rather than measuring directly from a blood sample. The sensor is placed on a thin part of the person's body, such as a fingertip or earlobe, and a light containing both red and infrared wavelengths is passed from one side to the other. The change in absorbance of each of the two wavelengths is measured and the difference used to estimate oxygen saturation of a person's blood and changes in blood volume in the skin. A photoplethysmogram (PPG) can then be obtained using the pulse oximeter sensor or with an optical sensor using a single light source. The PPG can be used to measure blood flow and heart rate. An electroencephelogram (EEG) can be monitored using electrodes attached to the scalp and measures voltages generated by brain activity.

The converter assembly 14 converts the electrical signals generated by the sensor assembly 12 to a frequency modulated ultrasonic signal that can be received by a computing device 16. In the embodiment shown in FIG. 5, the converter assembly 14 includes a converter 23 and an ultrasonic transmitter 24 for outputting frequency modulated ultrasonic signals having a carrier frequency in a range of from, for example, about 18 kHz to about 24 kHz. Nonlimiting examples of suitable ultrasonic transmitters 24 include, but are not limited to, miniature speakers, piezoelectric buzzers, and the like. The ultrasonic signals can be received by, for example, a microphone 25 in a computing device 16 such as a smartphone 30, personal digital assistant (PDA), tablet personal computer, pocket personal computer, notebook computer, desktop computer, server computer, and the like.

Prior art devices have used frequency modulated physiological signals to communicate between acquisition hardware and a computing device. The signals have a carrier frequency within the audible range such as the traditional 1.9 kHz FM frequency used to transmit ECG signals. However, it has been discovered that by using ultrasonic frequencies as the carrier, such as frequencies in the range of from about 18 kHz to about 24 kHz, and even 20 kHz to 24 kHz, the acoustic communication between the acquisition electronics 11 of the personal monitoring device 10, and a computing device 16 such as a smartphone, is virtually silent and far more noise-immune than the traditional 1.9 kHz FM ECG frequency. In fact, measurements of the audio signal power in the ultrasonic range determined that carrier frequencies of 17 kHz and higher provide communication that is immune to ambient and voice "noise" contamination. By using an ultrasonic carrier frequency, in even the "noisiest" environment, we create both a noise-free and a silent communication between the acquisition electronics 11 and the computing device 16 such as a smartphone 30, notebook computer, or the like.

Figure 7A:
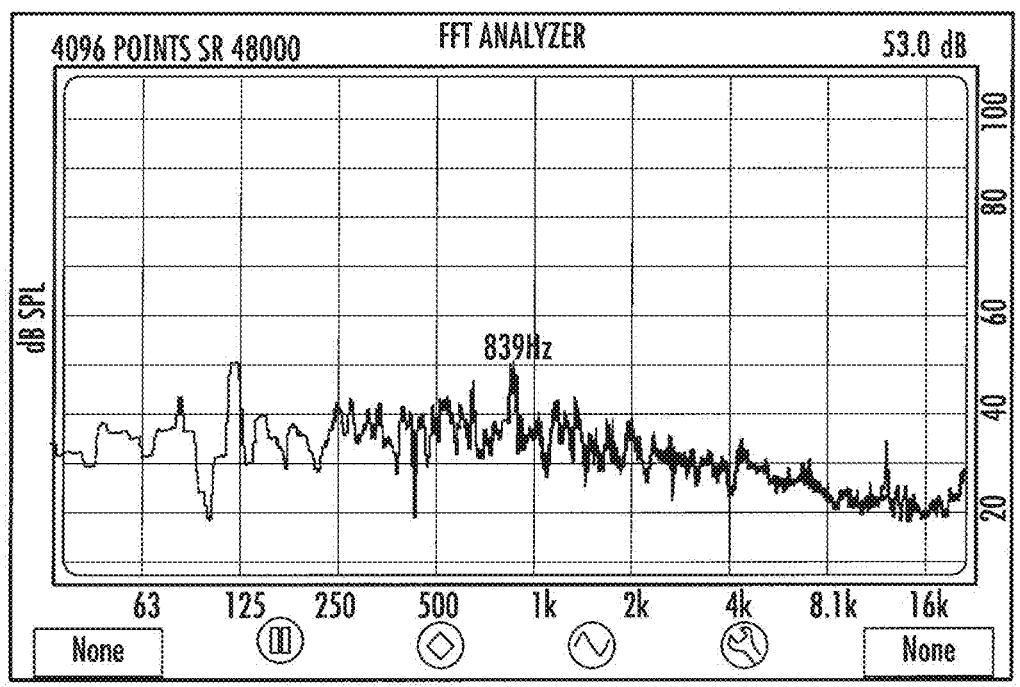
FIG. 7A is a spectrogram of the noise in a quiet office environment.
Figure 7B:
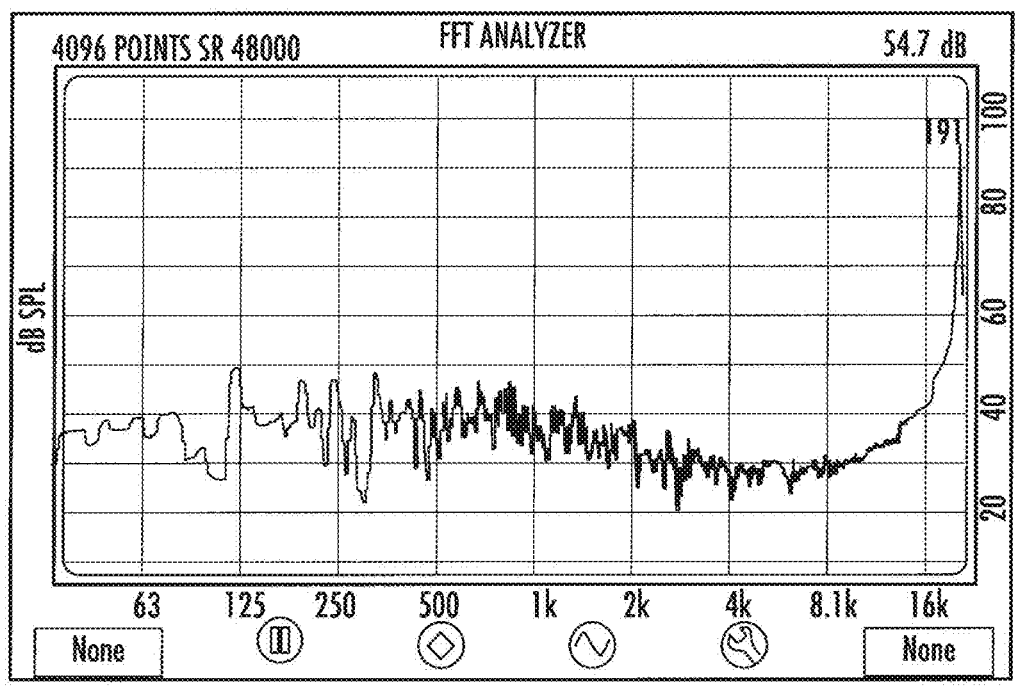
FIG. 7B is a spectrogram of a modulated ultrasonic signal from an ECG monitoring device embodied in the present invention.

For example, FIG. 7A shows a spectrogram of the sound in a quiet office environment. As can be seen, the ambient noise is about 35 dB at 2 kHz. FIG. 7B shows a spectrogram of the ultrasonic modulated ECG signal in the same quiet office environment. It should be noted that the ambient noise at 19 kHz is only 20 dB (the slight upturn is artifact) giving at least a 15 dB advantage for a 19 kHz ultrasonic signal compared to a standard 2 kHz signal. This is a significant improvement on the signal to noise ratio (SNR) which improves even more in noisy environments such as the street, shopping mall or a noisy home. Synergistically, the volume of the signal can be further increased at the ultrasonic frequencies, without concern for "listeners" present, because they cannot hear it.

In one embodiment, the personal monitoring device 10 is an ECG device 10' and includes an electrode assembly 18 configured to sense heart-related signals upon contact with a user's skin, and to convert the sensed heart-related signals to an ECG electric signal. As discussed in detail hereinafter, the ECG device 10' transmits an ultrasonic frequency modulated ECG signal to a computing device 16 such as, for example, a smartphone 30. Software running on the computer 16 or smartphone 30 digitizes and processes the audio in real-time, where the frequency modulated ECG signal is demodulated. The ECG can be further processed using algorithms to calculate heart rate and identify arrhythmias. The ECG, heart rate, and rhythm information can be displayed on the computer 16 or smartphone 30, stored locally for later retrieval, and/or transmitted in real-time to a web server 52 via a 2G/3G/4G, WiFi or other Internet connection. In addition to the display and local processing of the ECG data, the computer 16 or smartphone 30 can transmit, in real-time, the ECG, heart rate and rhythm data via a secure web connection for viewing, storage and further analysis via a web browser interface (using the 2G/3G/4G or WiFi connectivity of, for example, the smartphone 30). Server software provides for storage, further processing, real-time or retrospective display and formulation of a PDF ECG rhythm strip document and/or other reports and formats for printing remotely or locally.

In another embodiment, the converter assembly 14 of ECG device 10' is integrated with, and electrically connected to the electrode assembly 18 and is configured to convert the electric ECG signal generated by electrode assembly 18 to a frequency modulated ECG ultrasonic signal having a carrier frequency in the range of from about 18 kHz to about 24 kHz. It is sometimes desirable to utilize a carrier frequency in the 20 kHz to 24 kHz range. The ultrasonic range creates both a lower noise and a silent communication between the acquisition electronics 11 and the computing device 16 such as the smartphone 30, notebook, and the like.

Figure 8A:
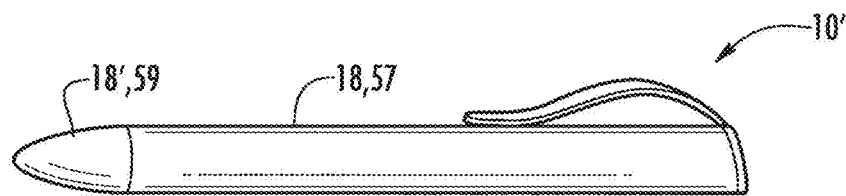
FIG. 8A is a schematic representation of an embodiment of a personal monitoring device of the present invention having a tubular shape.

The ECG device 10' can be configured in any way consistent with its function, i.e., it should include electrodes available to make contact with a user's skin on the hands, chest or other parts of the body, for obtaining the user's ECG, and means for transmitting the ECG using ultrasound to a receiving device. For example, a hand held ECG device 10' can be shaped like a credit card as in FIG. 5 with two electrodes on the bottom surface, or the ECG device 10' can be shaped like a flash light or pen as in FIG. 8A having one electrode 18 on the cylindrical surface 57 touching a holder's hand, and the other electrode 18' is on an end 59 contacting the chest, hand or other body part when in use.

Figure 8B:
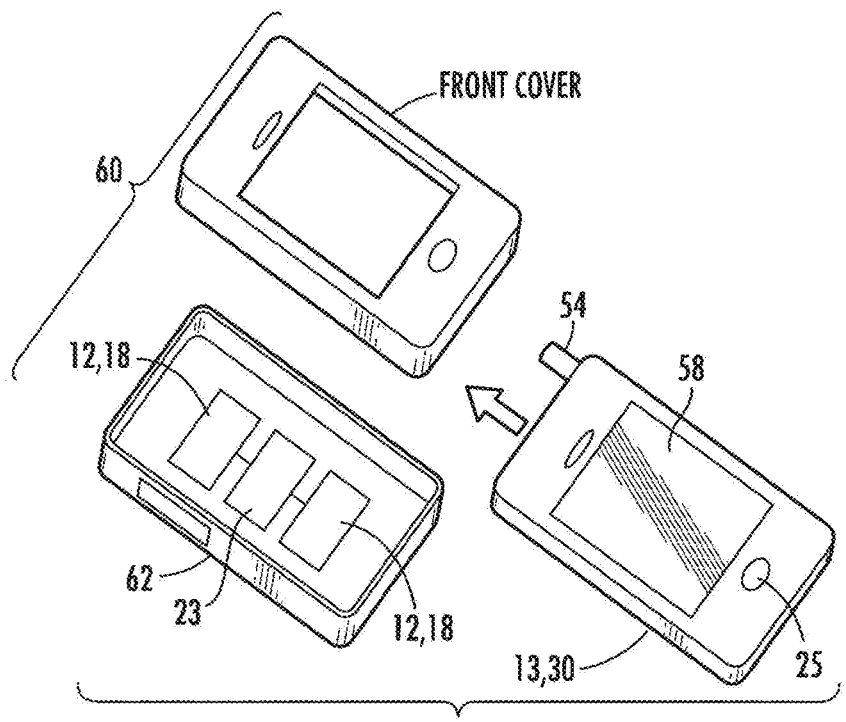
FIG. 8B is a schematic representation of another embodiment of a personal monitoring device of the present invention usable as a smartphone protective case.
Figure 8C:
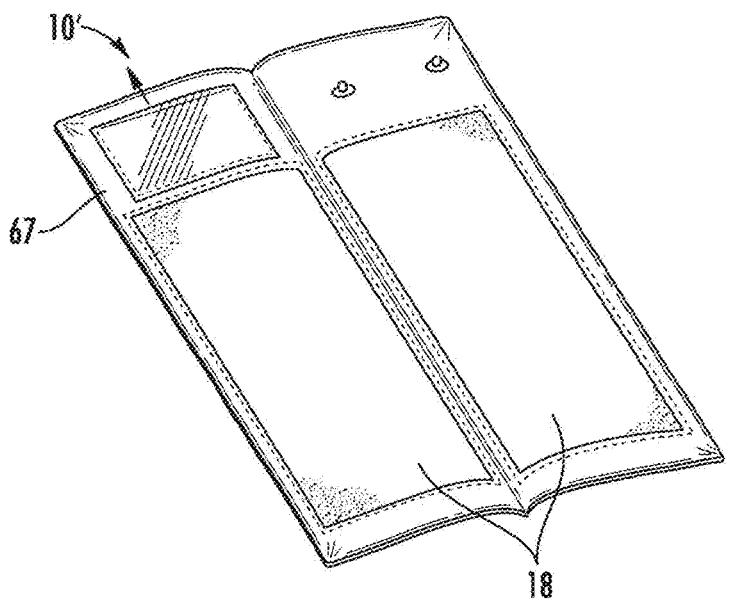
FIG. 8C is a schematic representation of an embodiment of a personal monitoring device of the present invention usable as a pad.

In another configuration, the ECG device 10' is usable as a smartphone protective case 60 as shown in FIG. 8B. One example configuration utilizes a "slip-on" protective case 60 for an iPhone® or other smartphone 30, the protective case 60 including an integrated ECG electrode assembly 18 and acquisition electronics 11 (2, 3 or 4 electrodes for generating a single lead of ECG data). The ECG electrodes are located on the side 62 of the case 60 opposite of the display screen 58. The smartphone 30, in its ECG-adapted protective case 60, can be held in both hands (generating a lead one, Left Arm minus Right Arm) or can be placed on a person's chest to generate a modified chest lead. The ECG is measured by the acquisition electronics 11 and converted into a frequency modulated ultrasonic signal. Nonlimiting example of suitable carrier or center frequencies include from about 18 kHz to about 24 kHz, or in some embodiments from about 20 kHz to 24 kHz. The frequency modulated ultrasonic signal is output by a miniature speaker 64 or a piezoelectric buzzer 66.

Figure 9A:
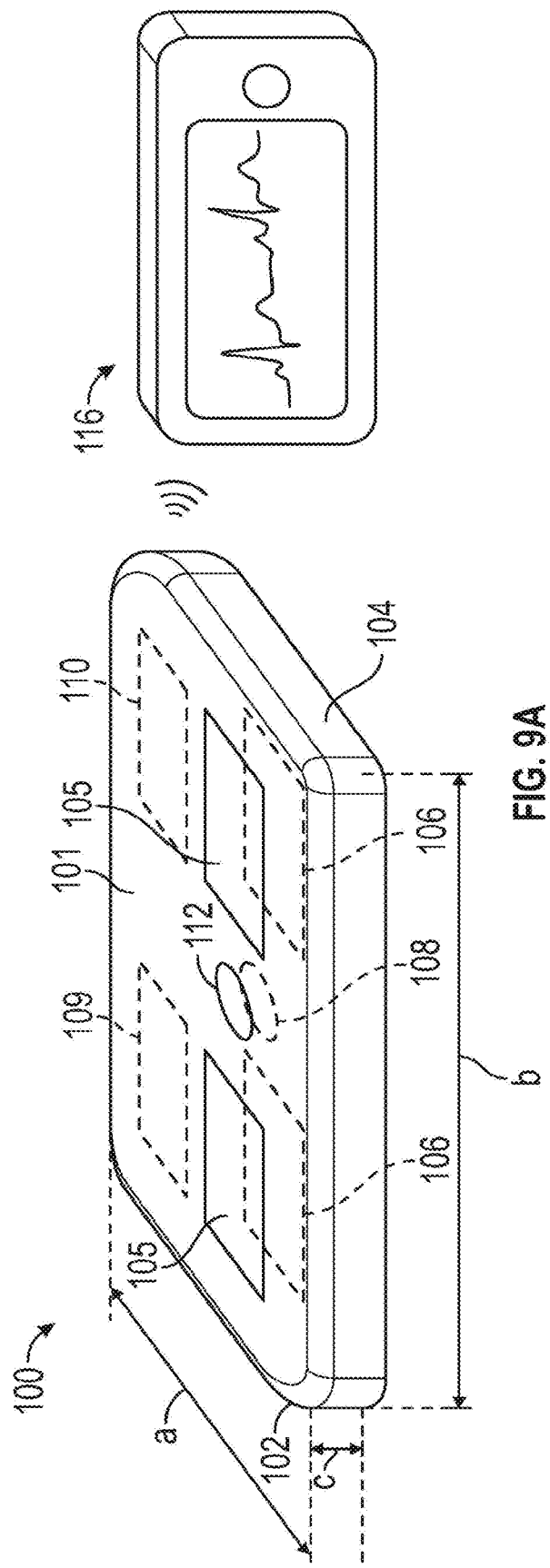
FIG. 9A is a perspective view of one embodiment of the present invention with a credit card form factor.

FIG. 9A shows another embodiment of a credit card like monitoring device 100 ("credit card sensor"), similar to that depicted as 10' in FIG. 5A, for remote or mobile acquisition of ECG data. Some embodiments may have a similar form as a financial bank or credit card, which may have a thickness of approximately 0.75 mm, and may be flexible and made of a plastic or polymer, such as polyvinyl chloride acetate (PVCA). Some embodiments of the credit card sensor have a thickness between 0.65 mm to 0.85 mm, and some between 0.70-0.78 mm. Some embodiments of the credit card sensor may have a range of bending stiffness, and some may meet the standards outlined by ISO 7810 ID-1 format. Embodiments of the credit card like senor may have a bending stiffness or flexibility permitting a user to place it in a purse or wallet in a similar manner to how a normal credit card is stored and carried.

Figure 9B:
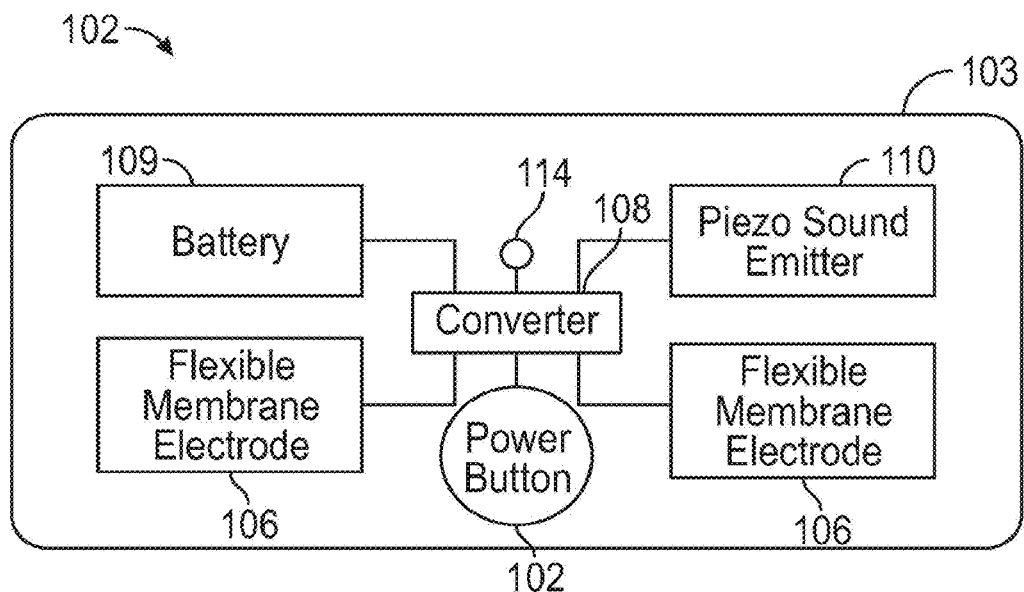
FIG. 9B depicts the underside of the upper layer of the embodiment of the present invention shown in FIG. 9A.
Figure 9C:
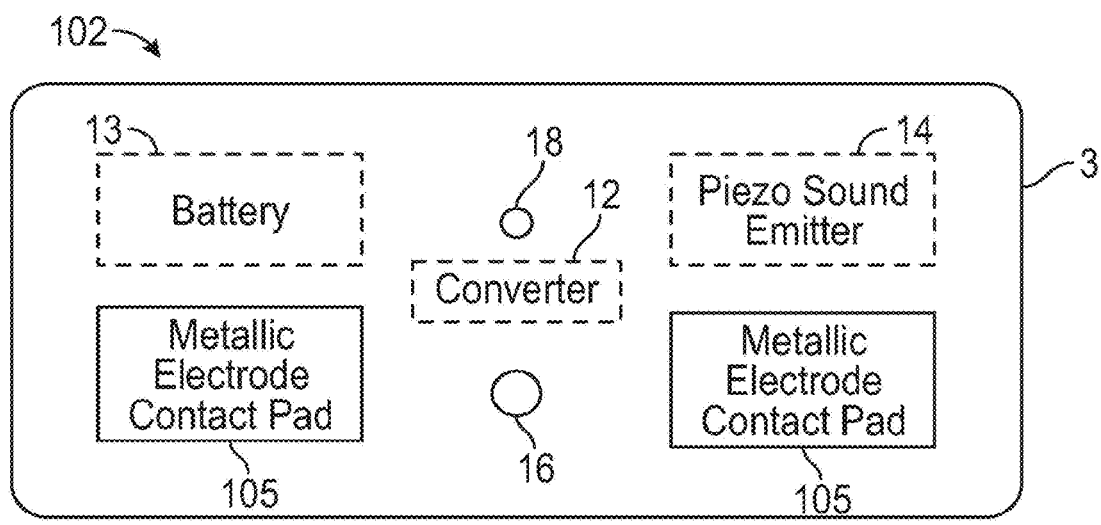
FIG. 9C depicts the topside of the upper layer of the embodiment of the present invention shown in FIG. 9A.

Referring to FIG. 9A, a perspective view of an embodiment of credit card sensor 100 is depicted. Credit card sensor 100 has a sandwich structure with upper layer 102 and lower layer 104, width a, length b and thickness c. FIG. 9B shows underside 103 of upper layer 102. Underside 103 has flexible membrane electrodes 106, one on each side of credit card sensor 100, converter 108, battery 109, piezo ultrasonic sound emitter 110, power button 112, and LED indicator 114. Battery 109 powers converter 108, which may be a printed circuit board with firmware installed thereon. FIG. 9C depicts topside 101 of upper layer 102. Topside 101 has exposed touch pads 105 that are in electrical contact with flexible membrane electrodes 106.

As described herein, a user contacts touch pads 105 (e.g., left and right fingers) that sense an electric signal for a Lead I ECG. Converter 108 converts the electrical signals generated from the touch pads 105 to a frequency modulated signal, for example an ultrasonic signal or Bluetooth signal (further described below), that can be received by a computing device 116. In the embodiment shown in FIGS. 9A-9C. The converter assembly includes a converter 108 and an ultrasonic transmitter 110 for outputting frequency modulated ultrasonic signals having a carrier frequency in a range of from, for example, about 18 kHz to about 24 kHz. The ultrasonic signals can be received by, for example, a microphone in computing device 116 such as a smartphone (as shown), personal digital assistant (PDA), tablet personal computer, pocket personal computer, notebook computer, desktop computer, server computer, smart watch or wearable, and the like. Computing device 116 has a microprocessor/CPU (not shown) that may do one or more of the following: acquire, digitize, demodulate, process and then display ECG data in real-time.

In an alternative embodiment, credit card sensor 100 may have a display (not shown) allowing near real time display of a user's ECG. In this embodiment, for example, credit card sensor 100 may include a receiver (not shown), which may be included with converter 108, that receives the processed ECG signal from the computing device and displays it on a display (not shown) on the credit card sensor 100. Alternatively, credit card sensor 100 may include a processor (not shown), which may be included with converter 108 having the ability to process and display the signals from touch pads 105 in a similar manner as the CPU of computing device 116. In this embodiment, all connections may be hard wired or wireless. Credit card sensor 100 may include memory (not shown), which may be part of or separate from converter 108, or the processor may include firmware (not shown), where the memory or firmware may include instructions for causing the processor to process the sensed heart-signals (e.g., ECG signals etc.) from a user contacting the touch pads 105 and displaying the heart-signals on a display (not shown) located on an exterior surface of credit card sensor 100. Transmitter 110 may be used to transmit the processed signal to a computing device, where a medical professional may view the recording. Alternatively, computing device, once in receipt of the data, may send the data to a medical professional using well know communications and data transfer technologies.

Figure 10:
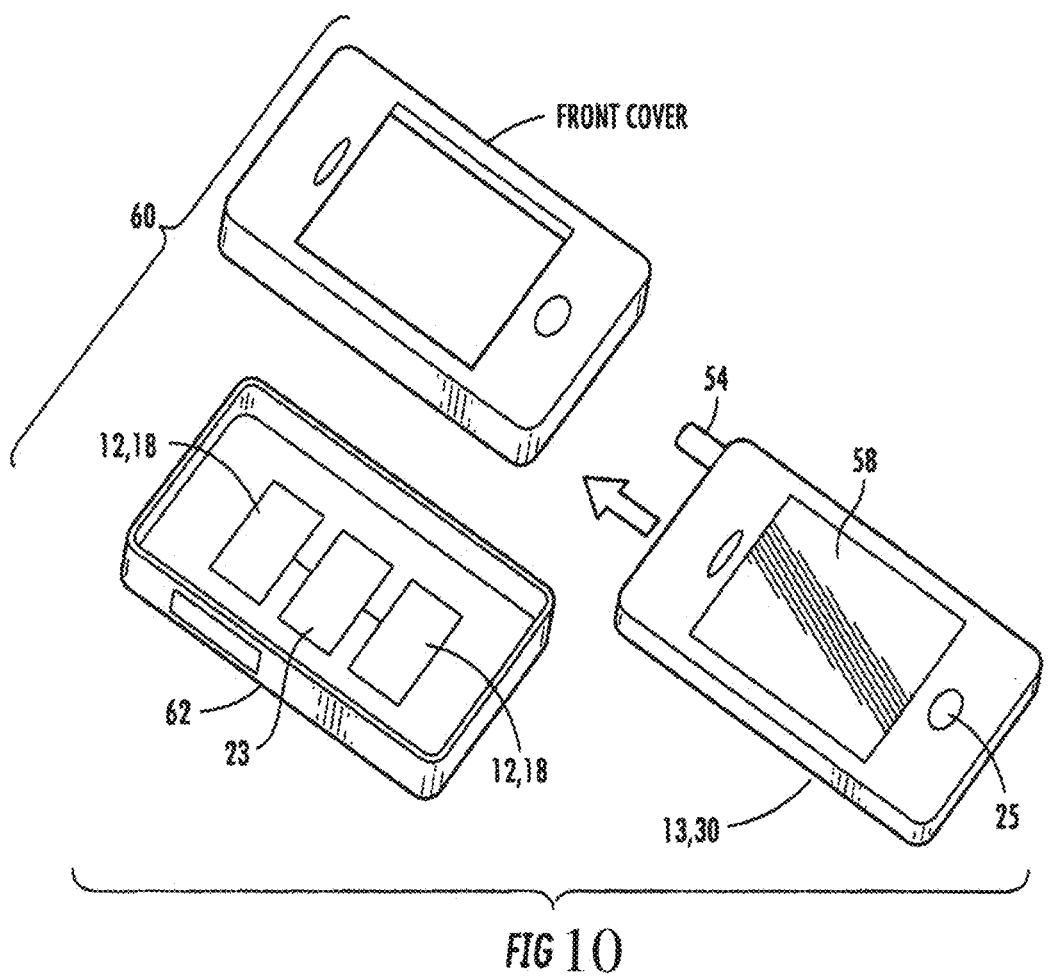
FIG. 10 is a perspective view of a personal monitoring device in accordance with one embodiment of the present invention.

In yet another embodiment, shown in FIGS. 10 (formerly 7 of '042) and 11 (formerly 8 of '042), converter assembly 108 includes a wireless radio transmitter 37 configured to convert and transmit the electrical signals generated by the sensor assembly 12 using a headset profile (HSP) of the Bluetooth® wireless communications standard is defined by the Bluetooth Special Interest Group (SIG) and available at URL address www.bluetooth.org. The electrical signals generated by the sensor assembly 12 are converted and transmitted using a Bluetooth® transceiver 34 and antenna 36 and communicated to the computing device 13, preferably a smartphone 30 or smart watch, according to instructions provided by a headset controller 38. Economy, as well as isolation and convenience, are provided by using a commercially available headset controller 38, Bluetooth® transceiver 34, and antenna 36, powered by a headset battery 40, wherein the electronics are commercially configured and mass-produced for communicating with computing devices 13 such as smartphones 30.

Computing device electronics 42 typically include a controller 44, a Bluetooth® transceiver 46 and antenna 48 for receiving input from a wireless Bluetooth® device. Most computing devices, and all smartphones and most wearables, include a memory 56, a display screen 58, and a transceiver 50 for transmitting/receiving information signals to/from a base station or web server 52 via a cellular antenna 54, or WiFi connection. Thus, the computing device electronics 42 can be used to store information from the personal monitoring device 10 in memory 56, and/or transmit the information to the base station 52 or a specific communication address via wireless communication technology well understood by those skilled in the art.

Figure 11:
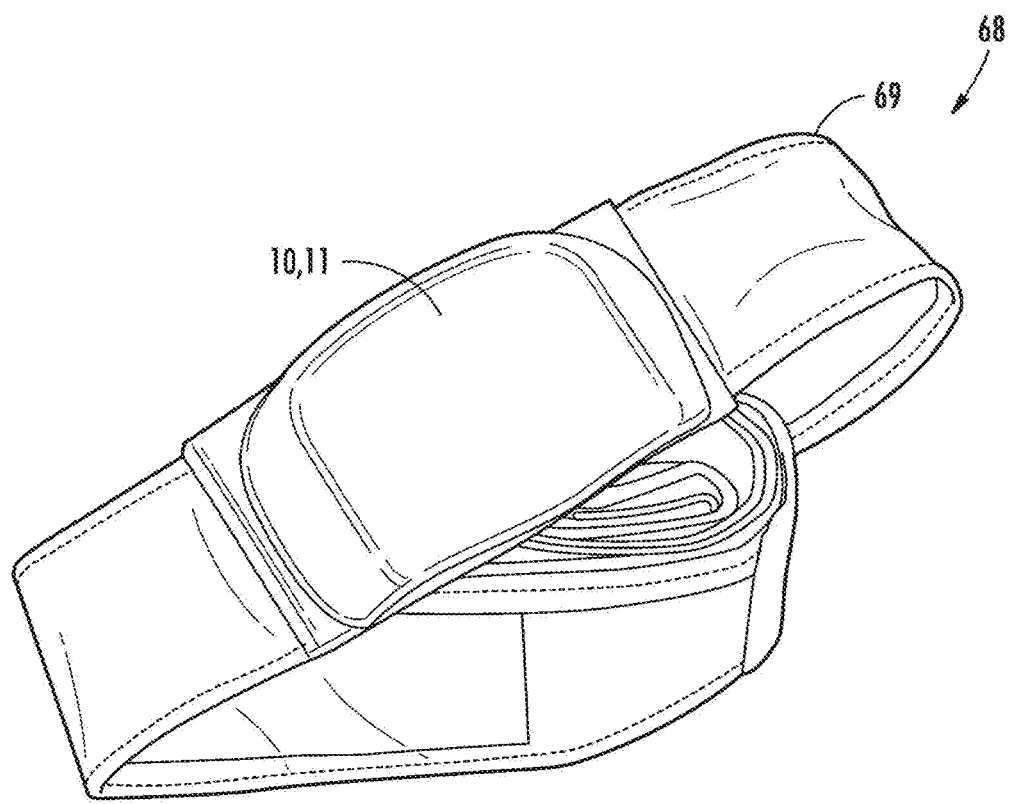
FIG. 11 is a schematic representation of an embodiment of an ECG device of the present invention included positioned within a chest strap.

In yet another embodiment, shown schematically in FIG. 11, the ECG device 10' is usable as a chest strap device 68 like a fitness heart rate monitor. The chest strap 69 with integrated ECG electrode assembly 18 and acquisition electronics 11 "pod" generate the frequency modulated ultrasonic ECG signal and send it to a computing device 16 such as the smartphone 30.

In any of the configurations, the computing device 16, such as smartphone 30, utilizes its built-in microphone 25 and CPU to acquire, digitize, demodulate, process and then display the ECG data in real-time. Also, the computing device 16, smartphone 30 or smart watch can calculate a real-time heart rate measurement and determine a cardiac rhythm diagnosis like atrial fibrillation. The computing device 16 or smartphone 30 can utilize its 2G, 3G, 4G, Bluetooth® and WiFi connectivity to transmit the ECG and other data to a secure web server 52 for real-time distant display, storage and analysis. Also, the ECG data can be stored locally on the smartphone 30 for later review or transmission.

Software on the smartphone 30 can also combine data and signals from other sensors built into the smartphone 30 such as a GPS and accelerometer. Further processing of this data provides additional information related to the user, such as speed, location, distance, steps, cadence, body position, fall detection and energy expenditure. The raw signals from the sensors and derived information can be displayed and stored locally on the smartphone 30, as well as being transmitted to the web server 52 over an internet connection. Software on the web server 52 provides a web browser interface for real-time or retrospective display of the signals and information received from the smartphone 30, and also includes further analysis and reporting.

Figure 12:
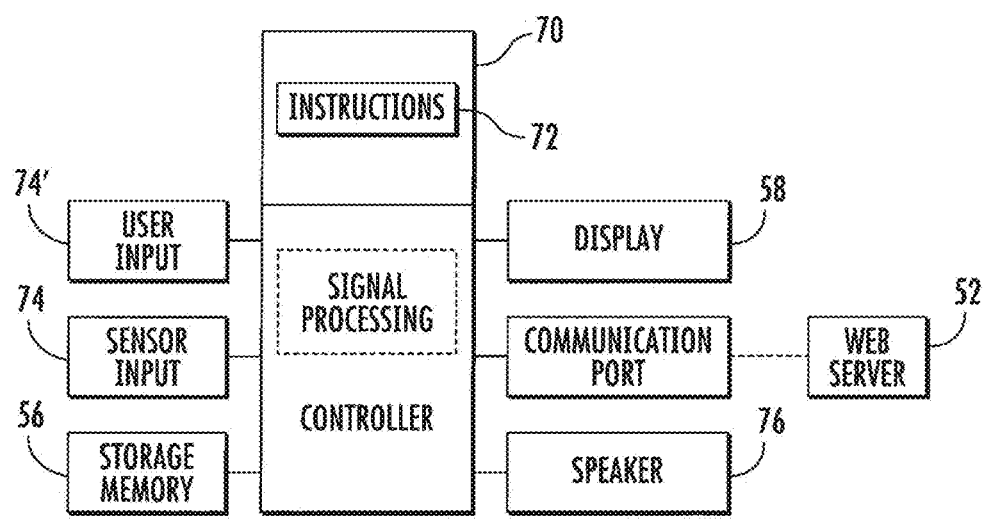
FIG. 12 is a schematic representation of a computer-readable storage medium embodiment of the present invention.

Referring now to FIG. 12, a computer-readable storage medium 56 stores a set of instructions 72, wherein the instructions 72 are capable of being executed by one or more computing devices 16. Nonlimiting examples of suitable computing devices 16 include smartphones 30, personal digital assistants (PDAs), tablet personal computers, pocket personal computers, notebook computers, desktop computers, and server computers. When the instructions 72 are executed, the one or more computing devices 16 is caused to digitize and demodulate a sensor input 74 such as an ultrasonic frequency modulated ECG signal to produce real-time demodulated digital ECG data. The instructions 72 can also cause the real-time demodulated digital ECG data to display on a display screen 58 of the computing device 16.

A common technique used for FM demodulation is based on zero crossing detection where the time interval between zero crossings is used to calculate the frequency and reconstruct the demodulated signal. In some applications simply counting the number of audio samples between zero crossings may provide sufficient accuracy for frequency estimation. Accuracy can be improved by interpolating between samples which provides a better estimate of the zero crossing point and subsequent frequency estimation. FM demodulation based on zero crossing detection is simple to implement and requires little computation compared with other techniques such as those using FFT's (fast Fourier transforms), making it particularly suitable for use in real-time applications on low power portable computing devices.

However, if the FM narrow band signal is close to the Nyquist frequency of the digitally sampled audio, the error in the zero crossing estimates become large, as there are very few samples per cycle. This severely limits the use of typical zero crossing demodulation techniques for ultrasonic carrier frequencies. An embodiment of the present disclosure provides a method to demodulate FM narrow band signals close to the Nyquist frequency, while maintaining the simplicity and efficiency of the zero crossing technique, with accurate frequency estimation.

Figure 13:
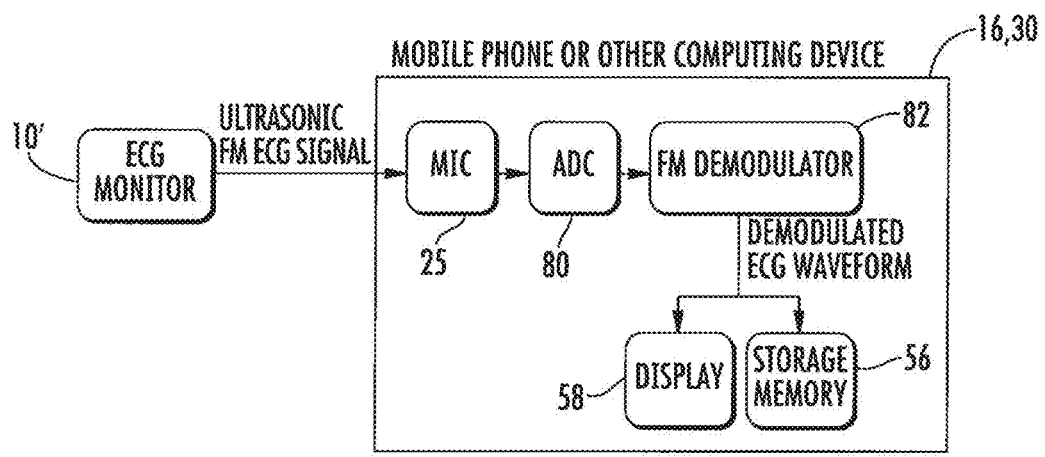
FIG. 13 is a schematic representation of an embodiment of the present invention.

Referring now to FIG. 13, an ultrasonic FM signal representing ECG signals is picked up by a microphone 25 in, for example, a mobile phone 30 or other computing device 16, and converted to an analog signal. The analog signal is continuous in time and is converted to a flow of digital values in an analog-to-digital converter 80, demodulated in FM demodulator 82 and shown on a display 58 of the smart phone 30 or other computing device 16, or retained in storage memory 56. Since a practical analog-to-digital converter 80, commonly referred to as an ADC, cannot make an instantaneous conversion, the input value must necessarily be held constant during the time that the converter performs a conversion. The rate at which the new digital values are sampled from the analog signal is called the sampling rate or sampling frequency of the ADC. Mobile phones and other personal computing devices are typically limited to recording audio at 44 kHz. Some smart phones such as ANDROID® and IPHONE® can sample at 48 KHz.

Figure 14:
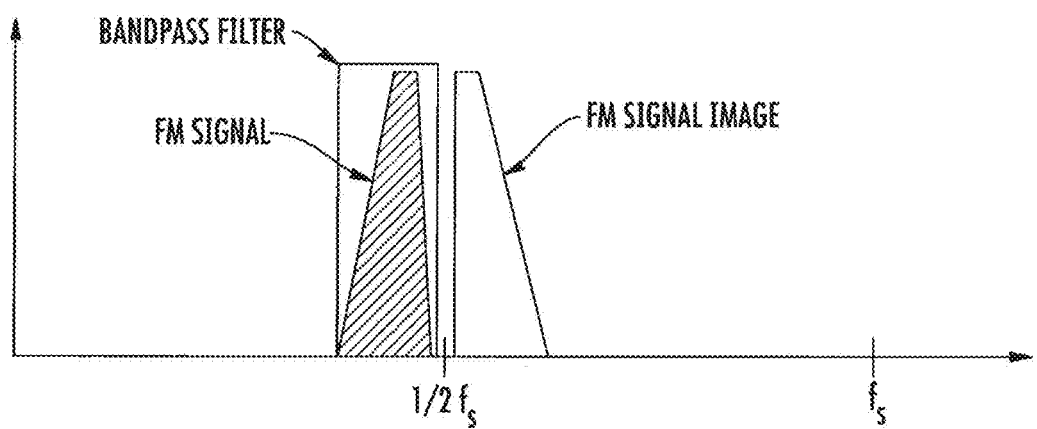
FIG. 14 is an example representation of a frequency spectrum after bandpass filtering.
Figure 15:
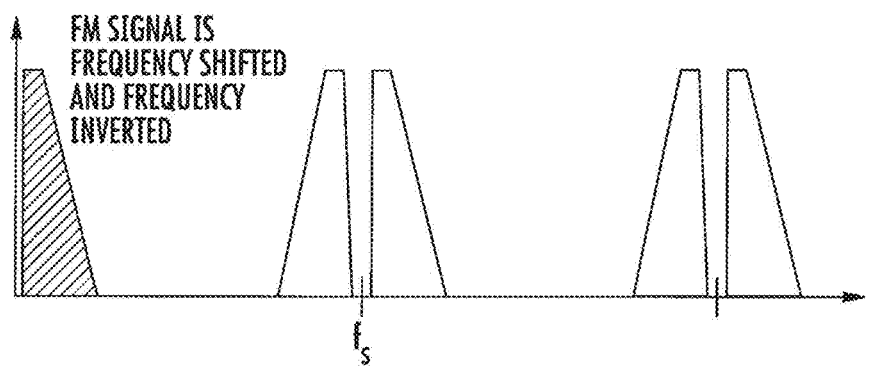
FIG. 15 is an example representation of a frequency spectrum after under-sampling at half the original sampling rate.

The digitized ultrasonic signal can then be bandpass filtered around the ultrasonic carrier frequency of the FM signal to improve signal-to-noise and reduce unwanted audio outside the passband. The filtered FM signal, as depicted in FIG. 14, is then "under-sampled" at half the sampling rate of the original audio. This results in aliasing of the FM signal that shifts and inverts the frequency spectrum to a lower frequency band. The result of the frequency spectrum being inverted by the under-sampling operation, results in the demodulated output being inverted as depicted in FIG. 15. The inversion is corrected by simply converting the final demodulated output.

With the FM signal at a lower frequency there are more audio samples per cycle and demodulation processes, such as zero crossing estimates, are significantly more accurate. For example, the zero crossing detector identifies the zero crossings where the audio signal changes sign. The accuracy of the zero crossing point is further improved by linearly interpolating between samples either side of the zero crossing. Finally, the period between zero crossings is used to calculate an estimate of the frequency and reconstruct the demodulated signal. While the above-described demodulation procedure utilizes a zero crossing estimate, it is understood that other demodulation procedures can be utilized and that the accuracy of other demodulation procedures will also benefit from the under-sampling operation.

Example

Figure 16:
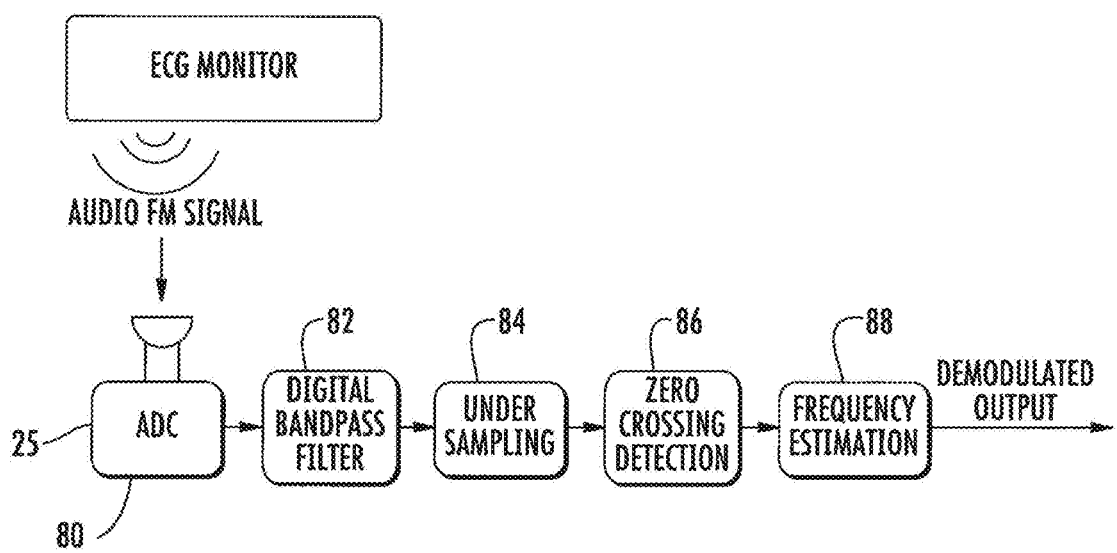
FIG. 16 illustrates a working example of a system for receiving and demodulating an ultrasonic FM ECG sound signal.

In one working example, illustrated in FIG. 16, a system used an ultrasonic FM ECG signal transmitted from a portable ECG monitor to a microphone 25 in a mobile phone 30 as well as a personal computer 16. This provided a low-cost wireless transmission solution that is compatible with most mobile phones and computers that have a microphone, without requiring any additional hardware to receive the signal.

It is desirable that the FM signal is above 18 kHz, so that it is inaudible to most people, does not interfere with music or speech, and is also less prone to audio interference. It is also desirable for the FM signal to have a narrow bandwidth to further reduce its susceptibility to audio interference. In this case the ECG monitor used an ultrasonic FM carrier of 19 kHz, modulated with an ECG at 200 Hz/mV and having a range of +5 mV. This resulted in an ultrasonic FM signal between 18 kHz and 20 kHz.

First, the audio FM signal was picked up by a microphone 25 and digitized by the ADC 80 in the mobile phone 30 at 44 kHz. The audio was then bandpass filtered in filter 82 between 18 kHz and 20 kHz to remove audio noise outside the pass band. In the next stage 84 the audio was under-sampled at 22 kHz, where only every second audio sample is used. The digital signal produced after such under-sampling results in aliasing that shifts and inverts the frequency spectrum so that it appears in the 2 kHz to 4 kHz range. A zero crossings detector 86 then identifies where the audio signal changes sign. The zero crossing point is then more accurately calculated in the frequency estimation step 88 by linearly interpolating between samples either side of the zero crossing. In this example, a frequency estimate is only required every 3.33 ms, for it demodulated output signal at 300 Hz. This is achieved by counting the number of zero crossings and measuring the period over the nearest fixed number of cycles during this period, providing a fixed 300 Hz output. The demodulated output is then inverted to correct for the frequency spectrum being inverted by the under-sampling operation. Finally, the 300 Hz demodulated ECG data is passed through a 40 Hz low pass filter since the ECG bandwidth of interest is below 40 Hz. This further reduces any noise from the frequency estimates and demodulated output. The FM demodulator outputs 16 bit, 300 Hz ECG.

Sensor input 74 can also include real-time information from additional sensors as well as user input 74'. For example, in embodiments wherein the computing device 16 is a smartphone 30, the input 74 can include real-time information from a GPS and/or accelerometer in the smartphone 30 in addition to the demodulated digital ECG data. User input 74' can also include spoken voice messages entered through a microphone of the computing device 16. Instructions 72 can cause the sensor and/or user input 74 and 74' to be recorded and maintained in a storage memory 56 of the computing device 16.

In one embodiment, the set of instructions 72, when executed by the one or more computing devices 16, can further cause the one or more computing devices 16 to calculate and display in real-time, a heart rate represented by the frequency modulated ECG ultrasonic signal. In addition, demodulated digital ECG data can be processed to identify the occurrence of an arrhythmia. In such designs, the storage medium 70 can include instructions 72 to cause the computing device 16 to display a warning on a display screen 58 or emit an audible alert through the speaker 76 at the occurrence of an arrhythmia.

Instructions 72 can cause the computing device 16 to store the demodulated digital ECG data in a memory 56 of the one or more computing devices 16 for later retrieval. The set of instructions 72 can further cause the one or more computing devices 16 to retrieve and transmit, upon demand, the stored demodulated digital ECG data to a web server 52 via an internet connection on the computing device 16. Recorded spoken voice messages can be stored and transmitted to the web server 52, simultaneously with the demodulated digital ECG data.

In other embodiments, the instructions 72 can cause the one or more computing devices 16 to transmit the demodulated digital ECG data, and/or voice messages, to the web server 52 in real-time.

A version of the smartphone software is packaged as a software library that can be integrated with other third party software applications. This provides a simplified and standard method for third party applications to use the ECG device 10' to obtain heart rate and other derived information without having to develop their own data acquisition, demodulation, and signal processing algorithms.

A version of the software also runs on a PC and includes demodulation, processing, storage and transmission to the web server 52. The software includes the audio acquisition, demodulation, ECG analysis, and acceleration analysis modules.

Audio samples from the ADC are optionally passed through a digital band-pass filter to remove unwanted frequencies outside the modulation range. The demodulation module demodulates the frequency modulated ECG ultrasonic signal using undersampling at about one-half the frequency of the audio sample to shift the spectrum to a lower frequency range, followed by a linear approximation and zero crossings algorithm. The demodulator allows selection of different modulation parameters to match the particular ECG device. While demodulation using zero crossings and linear approximation alone works well for carrier frequencies 6 kHz and lower, above 10 kHz with 44 kHz sampling, the errors from linear approximation become large unless undersampling is used to shift the spectrum.

The algorithm then looks at the sign of incoming data. When the sign changes it draws a straight line between the two points and interpolates the zero value. It uses this to determine the average frequency over a 3.333 ms interval, which provides ECG data at the output sampling rate of 300 Hz.

The ECG analysis module includes algorithms that process the ECG to detect and classify beats, and provides a heart rate estimate. Beat-to-beat heart rate is calculated from the interval between beats and a more robust measurement of heart rate is calculated using median filtering of the RR intervals.

The acceleration analysis module includes algorithms that process signals from the built-in 3 axis accelerometer sensor in the smartphone 30, to derive an estimate of a person's energy expenditure, steps, cadence, and body position and to detect falls.

Figure 17:
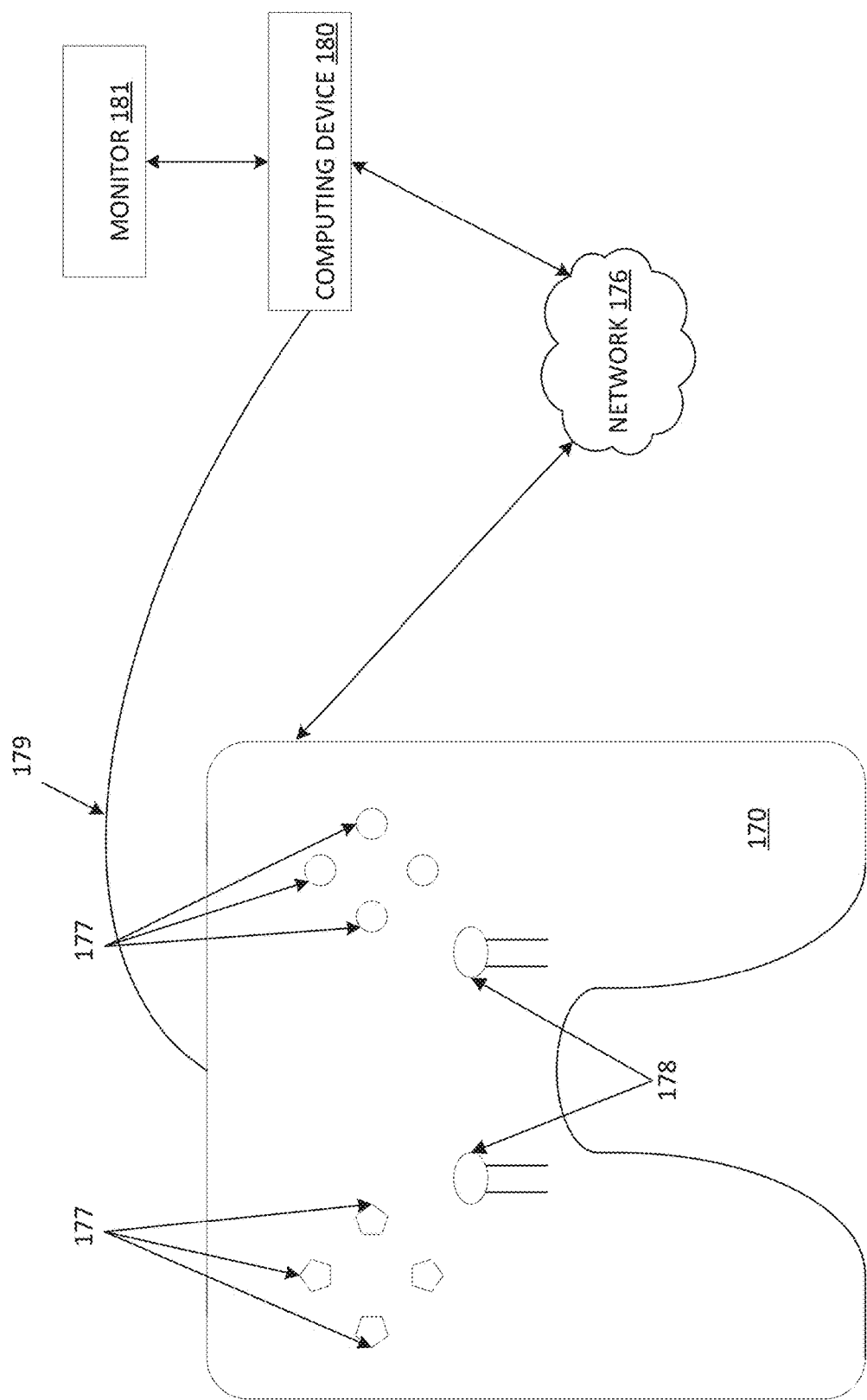
FIG. 17 illustrates a controller having integrated health monitoring apparatus in accordance with some embodiments of the present disclosure.
Figure 18B:
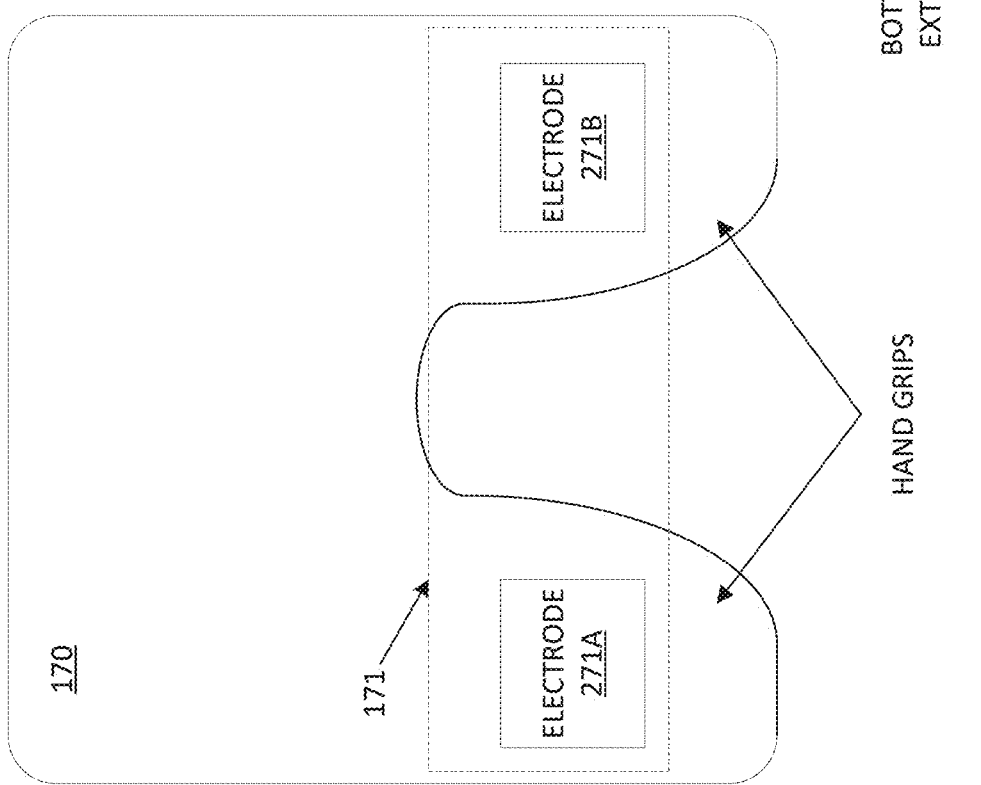
FIG. 18B depicts a bottom-view of the exterior surface of the controller of FIG. 17, in accordance with some embodiments of the present disclosure.
Figure 19:
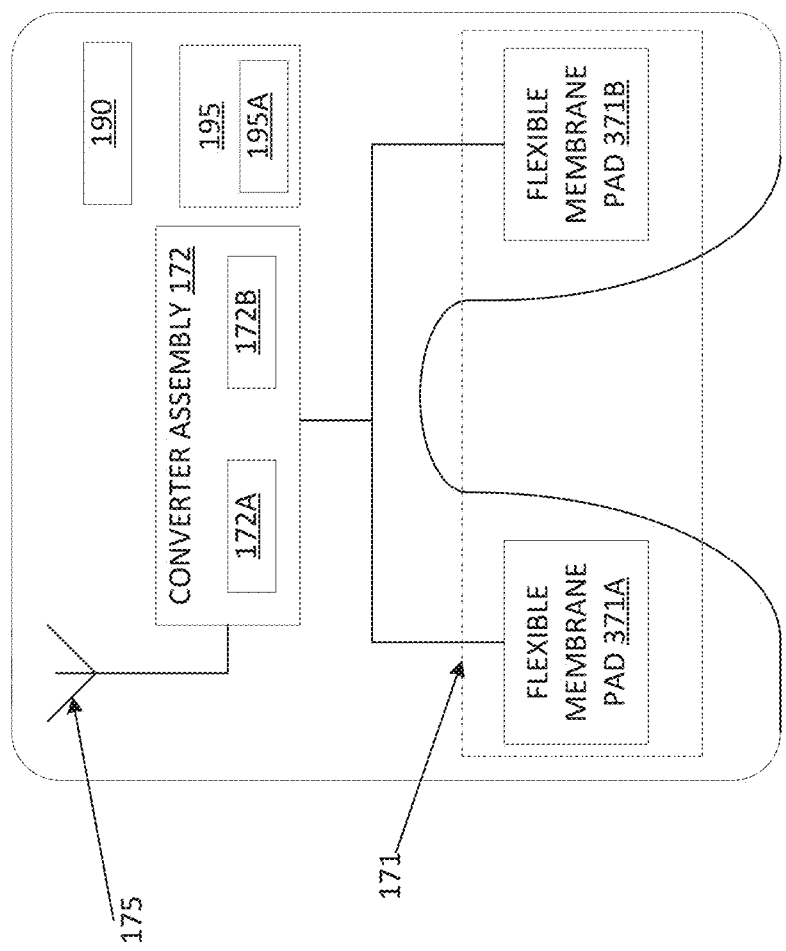
FIG. 19 depicts a hardware block diagram representing the interior of the controller of FIG. 17, in accordance with some embodiments of the present disclosure.

In some embodiments, the ECG device 10' may be implemented as a controller, which may be any appropriate device that communicates with and/or controls other computing devices. Examples of a controller may include a television remote control, a computer mouse, a keyboard, and bicycle handlebars. In one example, the controller may be a steering wheel that may communicate with/control e.g., an electronic control unit (ECU) or other on-board computing device of a vehicle. FIG. 17 illustrates an example in which a controller 170 may be a video game controller for controlling/utilizing computing device 180 (which may be a video game console in this example). It should be noted that computing device 180 may be similar to computing device 16 described herein. The controller 170 may include an electrode assembly 171 (as illustrated in FIG. 18B) which comprises a set of electrodes to sense electrical signals corresponding to electrical activity of the heart of the user over time and output the electrical signals (e.g., perform an ECG). For example, in response to the user grasping the hand grips of the controller 170, the electrode assembly 171 may begin performing an ECG of the user. The controller 170 may further include a converter assembly 172 (as illustrated in FIG. 19) to convert the electrical signals output by electrode assembly 171 to a frequency modulated signal (as discussed in further detail herein). The electrode assembly 171 may be similar to the electrode assembly 18 (illustrated in FIG. 5) and the converter assembly 172 may be similar to the converter assembly 14 or 108 (illustrated in FIGS. 5 and 9A respectively).

The converter assembly 172 may comprise a converter 173 to convert the electrical signals measured by electrode assembly 171 to a frequency modulated signal and a transmitter 174 to transmit the modulated signal to the computing device 180. In some embodiments, the transmitter 174 may be an ultrasonic transmitter that may transmit the modulated signal as an audio signal to the computing device 180 as discussed in further detail herein. In other embodiments, the transmitter 174 may be a Bluetooth transmitter to transmit the modulated signal as a Bluetooth signal to the computing device. In some embodiments, in addition to or as an alternative to the transmitter 174, the controller 170 may include a wireless transmitter 175 (shown in FIG. 19) that is coupled to the converter assembly 172. The controller 170 may be communicatively coupled to the computing device 180 via network 176 and may transmit the modulated signal to the computing device 180 via network 176 using the wireless transmitter 175.

Network 176 may be a public network (e.g., the internet), a private network (e.g., a local area network (LAN) or wide area network (WAN)), or a combination thereof. In one embodiment, network 176 may include a wired or a wireless infrastructure, which may be provided by one or more wireless communications systems, such as a Wi-Fi hotspot connected with the network 176 and/or a wireless carrier system that can be implemented using various data processing equipment, communication towers (e.g. cell towers), etc. In some embodiments, the network 176 may be an L3 network. The network 176 may carry communications (e.g., data, message, packets, frames, etc.) between the controller 170 and computing device 180.

In other embodiments, the controller 170 may be coupled to the computing device 116 via a cable 179, implementing any appropriate transmission protocol such as e.g., the USB™ protocol, and may transmit the modulated signal to the computing device 180 via the cable 179. The computing device 180 may include a receiver (not shown) for receiving the modulated signal, as well as a microprocessor/CPU (not shown) that may acquire, digitize, demodulate, and process the modulated signal to generate ECG data. Once the modulated signal is converted into ECG data, it can be displayed in real-time on a monitor 181 connected to the computing device 180. The ECG data can be displayed during use of the controller 170 as long as the user is contacting the electrode assembly 171. The computing device 180 may also analyze the ECG data to determine whether the user is experiencing a heart condition such as arrhythmia, bradycardia, and tachycardia, for example. The computing device 180 may utilize any of a number of appropriate algorithms for making this determination. In response to determining that the user is experiencing any of the above heart conditions, the computing device 180 may display an alert to the user, and take other actions such as notify a physician of the user, or stop a video game in progress (e.g., when the controller 170 is a video game controller), or instruct the user to pull over the side of the road (e.g., when the controller 170 is a steering wheel).

In some embodiments, the computing device 180 may include an application (not shown) to allow the ECG data to be displayed and evaluated in real-time directly on the computing device 180. For example, ECG data can be reviewed in the application once uploaded and the application may allow the console to show users their heart rate and rhythm information onscreen during gameplay or on demand. The application may handle performance of other functions as well such as e.g., analyzing the ECG data to determine whether the user is experiencing a heart condition, displaying an on-screen alert to the user in response to determining that the user is experiencing any of the above heart conditions, and/or notify a physician of the user in response to determining that the user is experiencing any of the above heart conditions, etc.

In some embodiments, the computing device 180 may utilize the ECG data to control aspects of a video game being played by the user. For example, the computing device 180 may utilize the ECG data to control aspects of the video game such as movement of characters within the video game. More specifically, the user's video game character may move slowly when the user's heart rate is low, but may move more quickly when the user's heart rate is high. If the user's heart rate has been high for a particular period of time, the character may gradually begin to slow down/become increasingly fatigued. In other examples, the user's video game character may be visibly nervous/upset/anxious when the user's heart rate accelerates. Other aspects of the video game may also be affected. For example, the music of the video game may speed up as the ECG data indicates the user's heart rate increasing and may slow down as the ECG data indicates the user's heart rate decreasing.

Figure 18A:
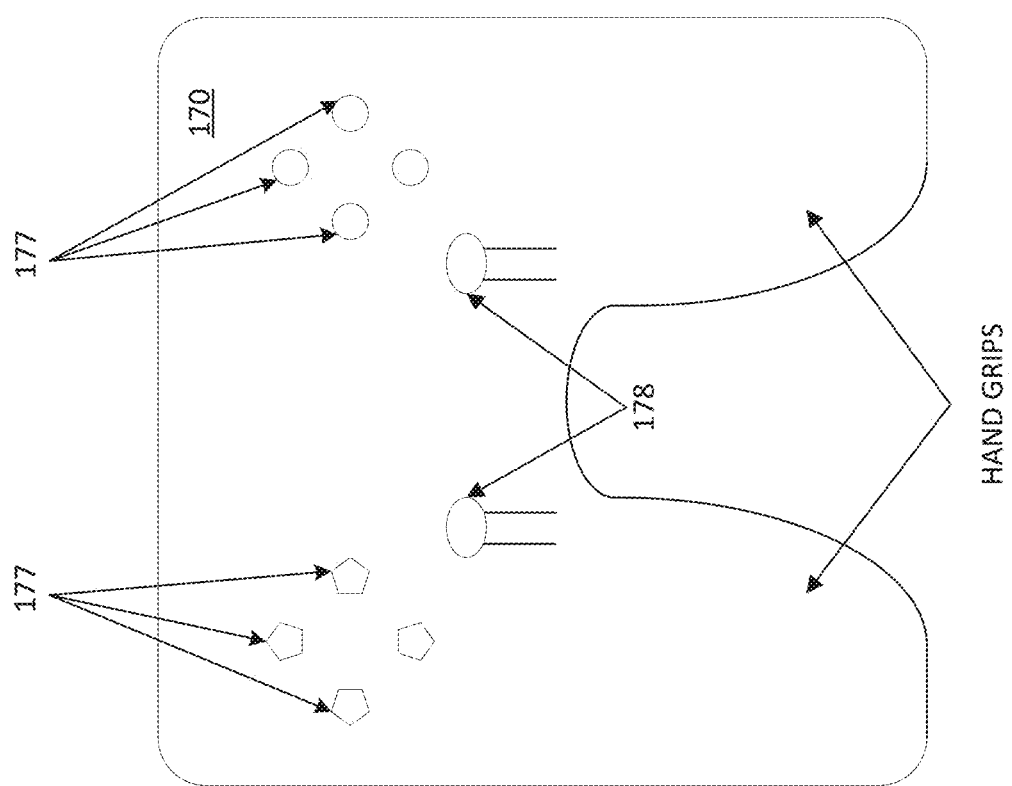
FIG. 18A depicts a top-view of the exterior surface of the controller of FIG. 17, in accordance with some embodiments of the present disclosure.

FIG. 18A displays the top view of the exterior surface (i.e., displays a top portion of the exterior surface) of the controller 170 where the buttons 177 and joysticks 178 used to provide signals to control the computing device 180 (e.g., play a game on the gaming console 180) are located. FIG. 18B displays the bottom view of the exterior surface (i.e., displays a bottom portion of the exterior surface) of the controller 170. As illustrated in FIG. 18B, the electrode assembly 171 may comprise a set of electrodes 271 (e.g., 271A and 271B) located on the bottom portion of the exterior surface, and more specifically, on the bottom of the hand grips of the controller 170. When the user is using the controller 170 to operate the computing device 180 (e.g., play a video game), the user's skin may maintain contact with the electrodes 271A and 271B which allows for electrical signals corresponding to electrical activity of the user's heart to be recorded. As shown in FIG. 18B, the electrode assembly 171 may include two electrodes 271A and 271B, providing a single lead ECG measurement. The electrodes 271 may be integrated to the controller 170 using any appropriate means. For example, the electrodes 271 may be made of conductive metal (e.g., stainless steel) that is attached to the exterior surface of the controller 170. In other examples, the electrodes 271 may be fabricated using conductive ink, which is then deposited onto the exterior surface of the controller 170. The conductive ink may be deposited onto the exterior surface of the controller 170 in such a fashion that the user is not aware of the presence of the electrodes 271 during operation of the controller 170. Although illustrated as located on the bottom portion of the exterior surface, the electrodes 271 may be positioned at any appropriate position where the user's hands will be relatively stable, and minimize motion artifacts caused by muscular movement (e.g., joysticks 178). It should be noted that although illustrated on the external surface of the controller 170, the electrode assembly 171 may include components that are located both on the exterior surface and the interior of the controller 170.

Although illustrated in FIG. 18B as having two electrodes 271A and 271B, the controller 170 (and, more specifically the electrode assembly 171) may comprise any appropriate number of electrodes 271. In some embodiments, the electrode assembly 171 may comprise three electrodes 271. The third electrode 271 may be located e.g., in the center of the bottom portion of the exterior surface of the controller 170, where it may make contact with the left leg, right leg, or any appropriate extremity/contact point on the left or right side of the body of the user. In this way, the third electrode 271C may provide a third contact point thereby allowing additional leads to be measured when taking an ECG. This may result in increased accuracy when taking the ECG.

Figure 18C:
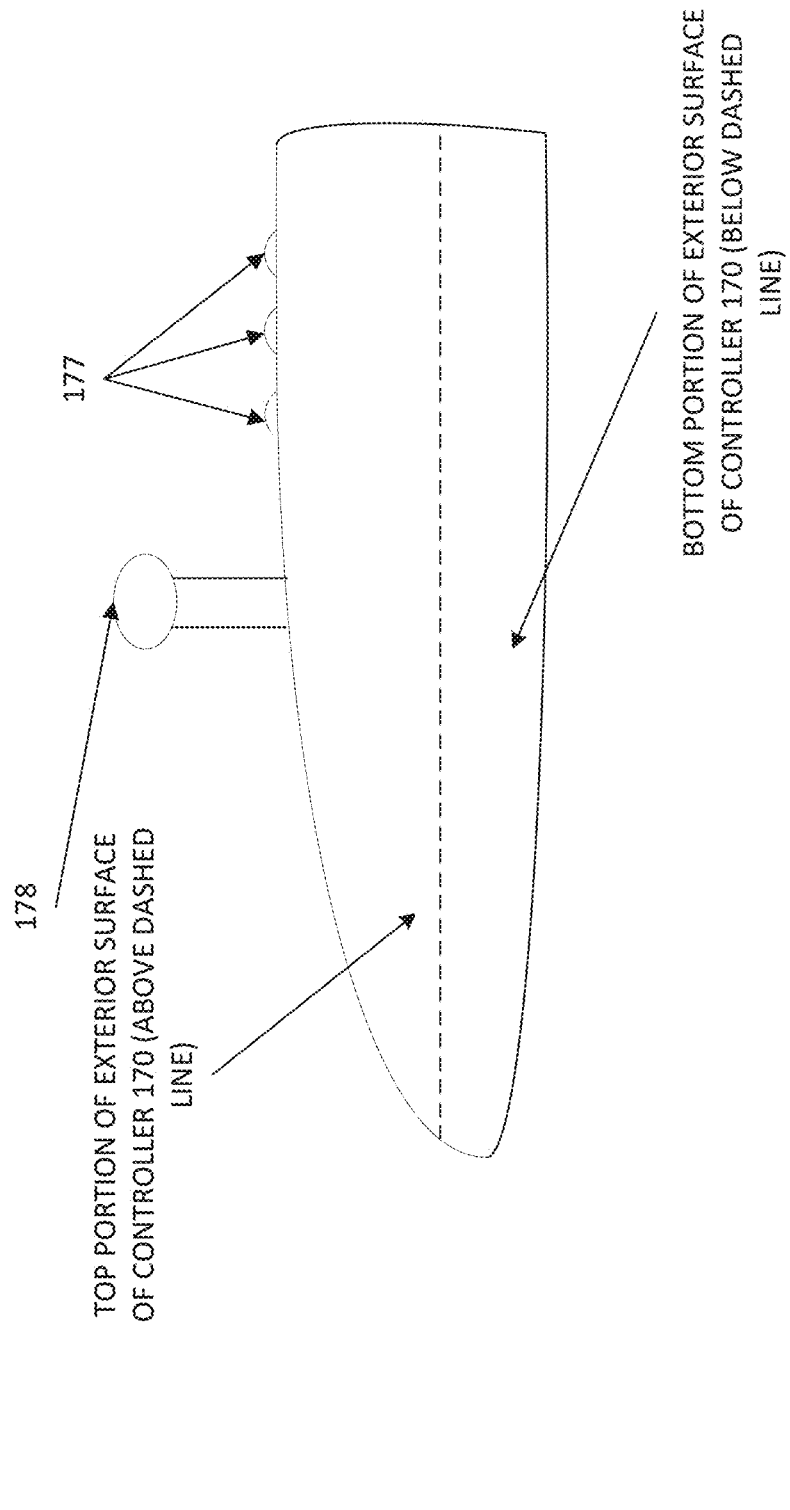
FIG. 18C depicts a side-view of the controller of FIG. 17 to distinguish the top and bottom portions of the exterior surface of the controller, in accordance with some embodiments of the present disclosure.

FIG. 18C illustrates a side view of the controller 170 in order to distinguish where the top and the bottom portions of the exterior surface of the controller 170 start and end. This view of the controller 170 shows the top part of the exterior surface of the controller 170 where the buttons 177 and joysticks 178 used to control the computing device 180 (e.g., play a game on the gaming console 180) are located. FIG. 18C also illustrates the bottom portion of the exterior surface of the gaming controller 170 where the electrode assembly 171 is located.

FIG. 19 illustrates an internal view of the gaming controller 170, including a hardware block diagram of the electrode assembly 171 (e.g., the internal portions thereof) and the converter assembly 172. As shown, the electrode assembly 171 further comprises flexible membrane pads 371A and 371B positioned within the hand grips, for example. Each flexible membrane pad 371 may be positioned under a corresponding electrode 271. In some embodiments, each flexible membrane pad 371 may be positioned directly under a corresponding electrode 271, while in other embodiments, the position of each flexible membrane pad 371 may be offset from the position of the corresponding electrode 271. Each flexible membrane pad 371 may be electrically connected to a corresponding electrode 271 and may receive the electrical signals sensed by the corresponding electrode 271. Each flexible membrane pad 371 may also be electrically coupled to the converter assembly 172 and may transmit the electrical signals sensed by the corresponding electrode 271 to the converter assembly 172 The converter assembly 172 may comprise a converter 172A to convert the electrical signals measured by the electrode assembly 171 into a modulated signal and a transmitter 172B. The transmitter 172B may output the modulated signal to the computing device 180 e.g., as an audio signal or Bluetooth signal. In some embodiments, the converter assembly 172 may provide the modulated signal to the wireless transmitter 175 which may transmit the modulated signal via network 170 to the computing device 180. Alternatively, the converter assembly 172 may transmit the modulated signal to the computing device 180 via cable 179.

Figure 20:
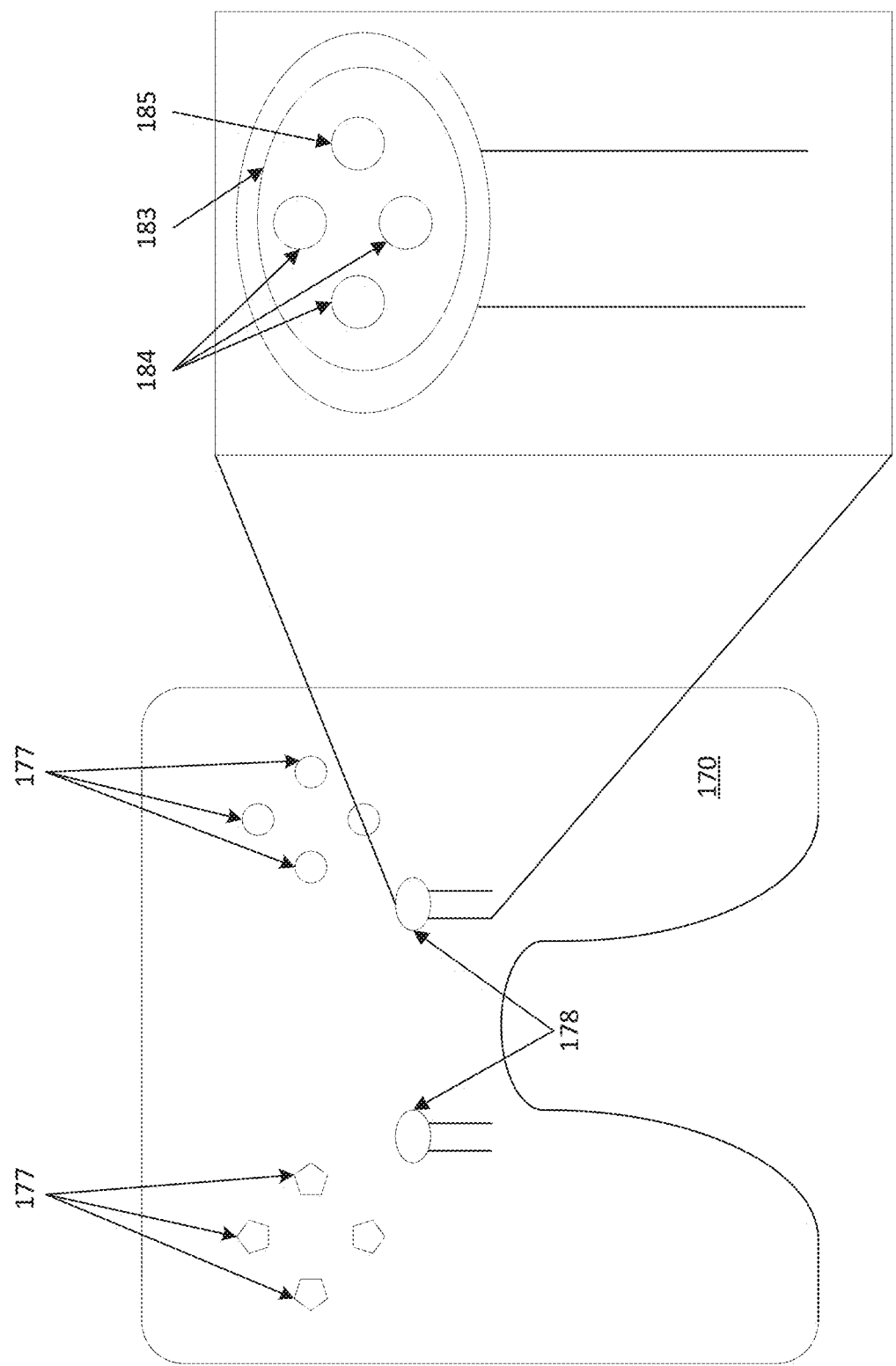
FIG. 20 is a perspective of a PPG sensor integrated into the controller of FIG. 17, in accordance with some embodiments of the present disclosure.

In some embodiments, the controller 170 may further comprise one or more PPG sensors 183 to measure PPG signals corresponding to additional health parameters of the user. Each PPG sensor 183 may be positioned on any appropriate location of the controller 170. FIG. 20 illustrates an embodiment of the present disclosure wherein a PPG sensor 183 is positioned on the top side of a joystick 178B on the controller 170. The PPG sensor 183 may comprise one or more light sources 184 (e.g., LEDs, photodiodes) and a photodetector 185. When the user places their fingertip (or any appropriate appendage) on the joystick 178, various additional health parameters of the user can be monitored indirectly in a noninvasive manner by passing, using the light sources 184, light (e.g., containing both red and infrared wavelengths) from one side of the user's fingertip to the other. The photodetector 185 may measure the change in absorbance of each of the two wavelengths and the difference may be used to estimate various additional health parameters such as the user's blood flow, heart rate, oxygen saturation of the user's blood, and changes in the blood volume in the user's skin. The PPG sensor 183 detect PPG signals corresponding to the change in absorbance of each of the two wavelengths and may output an electrical PPG signal representing the change in absorbance of each of the two wavelengths. Although discussed in terms of red and infrared wavelengths, light containing any combination of appropriate wavelengths may be used. The PPG sensor 183 may be electrically coupled to the converter assembly 172 and may output the electrical PPG signal to the converter assembly 172. The converter assembly 172 may convert the electrical PPG signal to a modulated PPG signal which is then output to the computing device 180 by the transmitter 172B. In some embodiments, the converter assembly 172 may output the modulated PPG signal to the wireless transmitter 175 which may transmit the modulated PPG signal to the computing device 180 via network 176. The computing device 180 may acquire, digitize, demodulate, and process the modulated PPG signal to determine the additional health parameters and display them as discussed herein.

The controller 170 may include other hardware such as processing device 190 (e.g., processors, central processing units (CPUs)) and memory 195 (e.g., random access memory (RAM), storage devices (e.g., hard-disk drive (HDD), solid-state drive (SSD), etc.)), and other hardware devices (e.g., sound card, video card, etc.). The memory 195 may store a health analysis module 195A which may be executed by the processing device 190 in order to instruct each of the other components of controller 170 to perform their functions as described herein. Although illustrated as separate components, in some embodiments the processing device 190 and the memory 195 may be part of one of the other components of controller 170, such as the converter assembly 172.

Figure 21:
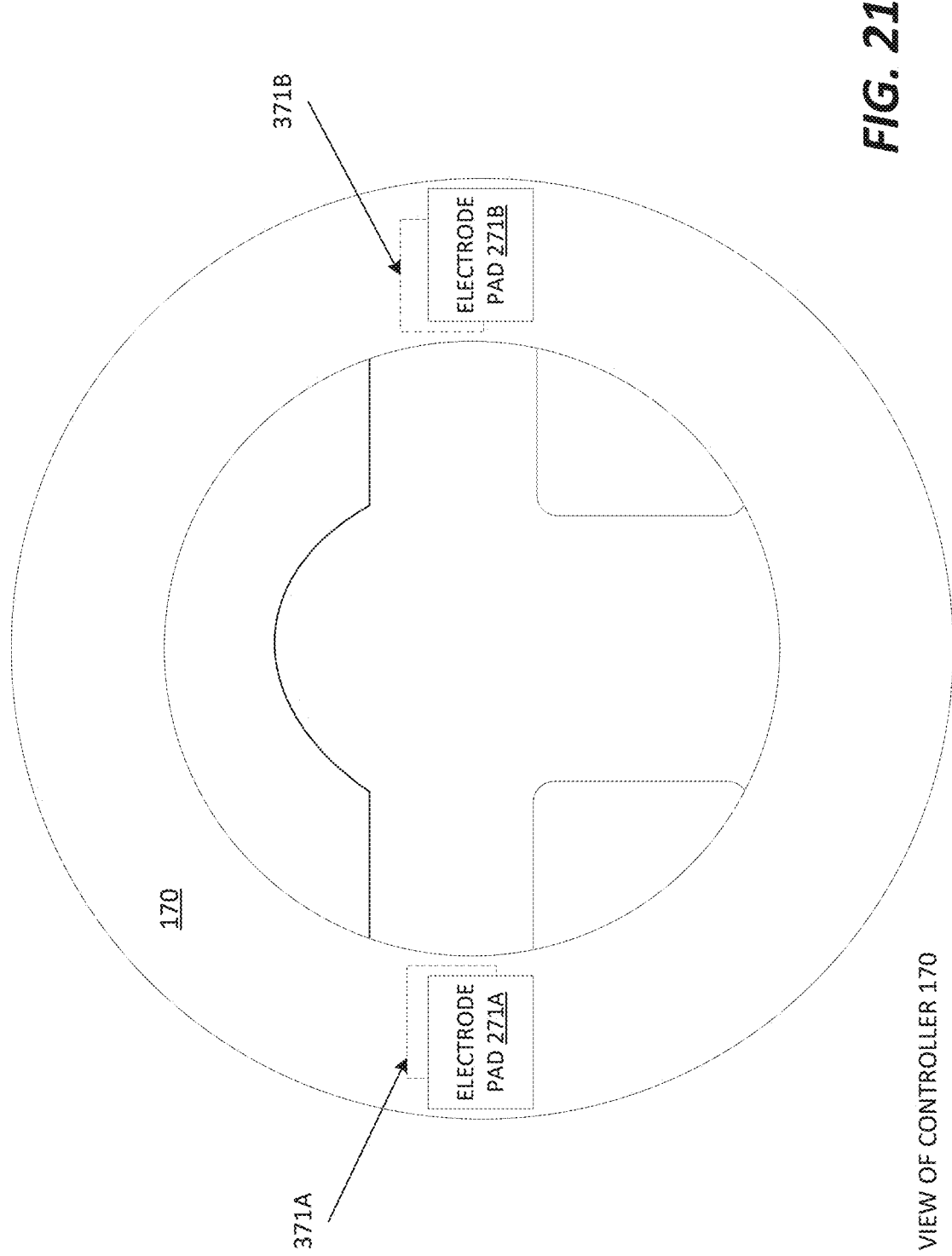
FIG. 21 is a perspective view of one embodiment of the present invention where the controller of FIG. 17 is implemented as a steering wheel.

FIG. 21 illustrates another embodiment of the present disclosure where the controller 170 is implemented as a steering wheel of a vehicle which may control/communicate with computing device 180 which may be e.g., an on board computer within the vehicle (not shown in the FIGS). The electrode assembly 171 may be implemented on the top portion of the exterior surface of the controller 170. The electrode assembly 171 may comprise the set of electrodes 271, each of which may be placed at locations on the exterior surface of the controller 170 where the user's hands will be relatively stable, and minimize motion artifacts caused by muscular movement. The positioning of the electrodes 271 may also account for places where the user is likely to position her/her hands while driving, for example at the "10 o'clock" and "2 o'clock" positions. As shown in the example of FIG. 21, the controller 170 may comprise two electrodes 271A and 271B that are placed on its right and left side (i.e., the right and left side of the steering wheel (e.g., at the 90 and 270 degree positions respectively). The electrode assembly 171 may further comprise the set of flexible membrane pads 371 located on the interior of the controller 170. In some embodiments, each flexible membrane pad 371 may be positioned directly under a corresponding electrode 271, while in other embodiments, the position of each flexible membrane pad 371 may be offset from the position of the corresponding electrode 271. The electrode assembly 171 (more specifically, the flexible membrane pads 371) may be electrically coupled to the converter assembly 172 which comprises the converter 172A and the transmitter 172B. The electrode assembly 171 and the converter assembly 172 may function as described herein (e.g., with respect to FIGS. 4-6, 17, 18A-C, and 19). In some embodiments, the controller 170 may further comprise one or more PPG sensors 183 to measure PPG signals corresponding to additional health parameters of the user as discussed above.

Continuing to refer to FIG. 21, in some embodiments the computing device 180 is an ECU or other onboard computing device of the vehicle, which can be partially or fully internal to the vehicle. The computing device 180 may include a receiver (not shown) for receiving the modulated signal, as well as a microprocessor/CPU (not shown) that may acquire, digitize, demodulate, and process the modulated signal to generate ECG data. The computing device 180 may include a display (not shown) to display the ECG data in real-time. Alternatively, the computing device 180 may be coupled to a display/monitor (not shown) which may be integrated into the dashboard of the vehicle, for example, and the ECG data can be displayed on the monitor. In some embodiments, the display may be a peripheral component that can be coupled to the computing device 180.

Figure 22:
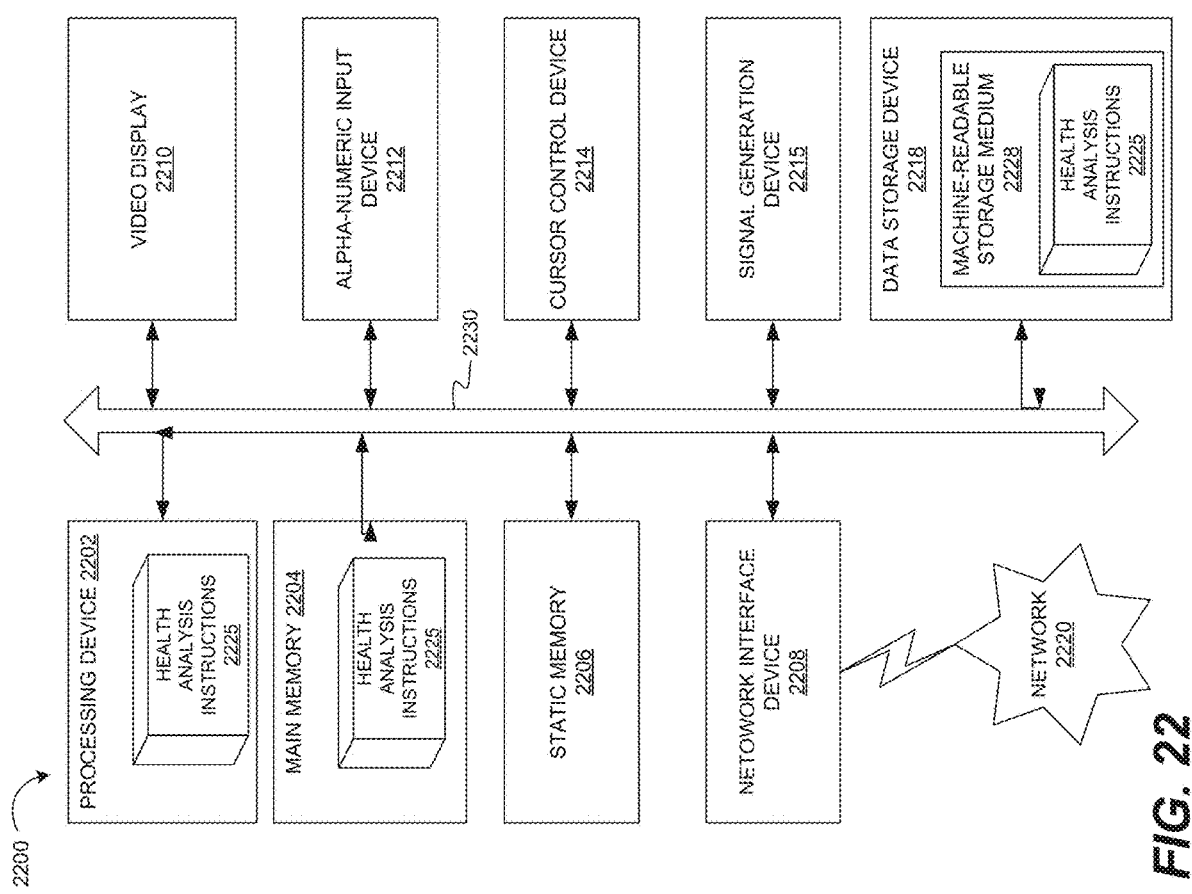
FIG. 22 is a diagram of a computing device, in accordance with some embodiments of the present disclosure.

FIG. 22 is a block diagram of an example computing device 2200 that may perform one or more of the operations described herein. Computing device 2200 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 2200 may include a processing device (e.g., a general purpose processor, a PLD, etc.) 2202, a main memory 2204 (e.g., synchronous dynamic random access memory (DRAM), read-only memory (ROM)), a static memory 2206 (e.g., flash memory and a data storage device 2218), which may communicate with each other via a bus 2230.

Processing device 2202 may be provided by one or more general-purpose processing devices such as a microprocessor, central processing unit, or the like. In an illustrative example, processing device 2202 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 2202 may also comprise one or more special-purpose processing devices such as an application specific integrated circuit (ASIC), a field programmable gate array (FPGA), a digital signal processor (DSP), network processor, or the like. The processing device 2202 may be configured to execute the operations described herein, in accordance with one or more aspects of the present disclosure, for performing the operations and steps discussed herein.

Computing device 2200 may further include a network interface device 2208 which may communicate with a network 2220. The computing device 2200 also may include a video display unit 2210 (e.g., a liquid crystal display (LCD) or a cathode ray tube (CRT)), an alphanumeric input device 2212 (e.g., a keyboard), a cursor control device 2214 (e.g., a mouse) and an acoustic signal generation device 22122 (e.g., a speaker). In one embodiment, video display unit 2210, alphanumeric input device 2212, and cursor control device 2214 may be combined into a single component or device (e.g., an LCD touch screen).

Data storage device 2218 may include a computer-readable storage medium 2228 on which may be stored one or more sets of health analysis instructions 2225, e.g., instructions for carrying out the operations described herein, in accordance with one or more aspects of the present disclosure. Health analysis instructions 2225 may also reside, completely or at least partially, within main memory 2204 and/or within processing device 2202 during execution thereof by computing device 2200, main memory 2204 and processing device 2202 also constituting computer-readable media. The health analysis instructions 2225 may further be transmitted or received over a network 2220 via network interface device 2208.

While computer-readable storage medium 2228 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:

1. A system comprising:
    a video game controller comprising:
        an electrode assembly comprising:
            a set of electrodes to sense an electrical signal corresponding to heart activity of a user when in contact with skin of the user and output the electrical signal; and
            a set of conductive flexible membranes, each conductive flexible membrane operatively coupled to a corresponding electrode of the set of electrodes;
        a converter assembly operatively coupled to the electrode assembly, the converter assembly to convert, by a processing device, the electrical signal to a modulated signal, wherein the modulated signal carries the electrical signal, wherein each conductive flexible membrane is also operatively coupled to the converter assembly; and
        a transmitter to transmit the modulated signal; and
    a computing device to receive the modulated signal and determine whether the electrical signal indicates that the user is experiencing a heart condition.

2. The system of claim 1, wherein the computing device is further to:
    process the modulated signal to generate ECG data of the user; and
    display the ECG data.

3. The system of claim 1, wherein a first electrode and a second electrode of the set of electrodes are positioned on an area of a bottom portion of an exterior surface of the video game controller where motion artifacts caused by muscular movement of the user while using the video game controller are minimized.

4. The system of claim 3, wherein a third electrode of the set of electrodes is positioned on the bottom portion of the exterior surface to provide additional leads for detecting the electrical signal.

5. The system of claim 1, wherein each of the set of electrodes comprises a conductive metal attached to an external surface of the video game controller.

6. The system of claim 1, wherein each of the set of electrodes comprises a conductive ink that is deposited onto an external surface of the video game controller.

7. The system of claim 1, wherein the video game controller further comprises:
one or more photoplethysmogram (PPG) sensors to detect a PPG signal corresponding to additional health-related parameters of the user and produce an electrical PPG signal representing the detected PPG signal, wherein the controller modulates the electrical PPG signal to generate a modulated PPG signal and transmits the modulated PPG signal to the computing device.

8. The system of claim 7, wherein the computing device is further to:
process the modulated PPG signal to determine the additional health related parameters of the user, the additional health-related parameters including a blood flow of the user, a heart rate of the user, a blood oxygen saturation of the user, and a change in blood volume in the skin of the user.

9. The system of claim 2, wherein the computing device is further to:
modify operation of a video game based on the ECG data.

10. The system of claim 9, wherein to modify the operation of the video game, the computing device is to alter a behavior of a character of the video game based on the ECG data.

11. The system of claim 9, wherein to modify the operation of the video game, the computing device is to alter music of the video game based on the ECG data.

12. An apparatus comprising:
a video game controller;
an electrode assembly integrated within the video game controller, the electrode assembly comprising a set of electrodes to sense an electrical signal corresponding to heart activity of a user when in contact with skin of the user and output the electrical signal, and wherein each of the set of electrodes comprises a conductive metal attached to an external surface of the video game controller;
a converter assembly integrated within the video game controller and operatively coupled to the electrode assembly, the converter assembly to convert, by a processing device, the electrical signal to a modulated signal, wherein the modulated signal carries the electrical signal; and
a transmitter integrated into the video game controller, the transmitter to transmit the modulated signal.

13. The apparatus of claim 12, wherein the electrode assembly further comprises a set of conductive flexible membranes, each conductive flexible membrane operatively coupled to a corresponding electrode of the set of electrodes and operatively coupled to the converter assembly.

14. The apparatus of claim 13, wherein a first electrode and a second electrode of the set of electrodes are positioned on an area of a bottom portion of an exterior surface of the video game controller where motion artifacts caused by muscular movement of the user while using the video game controller are minimized.

15. The apparatus of claim 14, wherein a third electrode of the set of electrodes is positioned on the bottom portion of the exterior surface to provide additional leads for detecting the electrical signal.

16. The apparatus of claim 12, wherein each of the set of electrodes comprises a conductive ink that is deposited onto an external surface of the video game controller.

17. The apparatus of claim 12, further comprising:
one or more photoplethysmogram (PPG) sensors to detect a PPG signal corresponding to additional health-related parameters of the user and produce an electrical PPG signal representing the detected PPG signal, wherein the video game controller modulates the electrical PPG signal to generate a modulated PPG signal and transmits the modulated PPG signal to the computing device.

18. The apparatus of claim 17, wherein the additional health-related parameters include a blood flow of the user, a heart rate of the user, a blood oxygen saturation of the user, and a change in blood volume in the skin of the user.

* * * * *